(12) United States Patent
Hayama

(10) Patent No.: US 7,827,189 B2
(45) Date of Patent: Nov. 2, 2010

(54) SENSE DATABASE

(75) Inventor: Masahide Hayama, Yokohama (JP)

(73) Assignee: Ajikaori Senryaku Kenkyusyo Co., Ltd., Yokohama-shi (JP)

(*) Notice: Subject to any disclaimer, the term of this patent is extended or adjusted under 35 U.S.C. 154(b) by 601 days.

(21) Appl. No.: 11/596,101

(22) PCT Filed: May 12, 2004

(86) PCT No.: PCT/JP2004/006398

§ 371 (c)(1),
(2), (4) Date: Sep. 20, 2007

(87) PCT Pub. No.: WO2005/109246

PCT Pub. Date: Nov. 17, 2005

(65) Prior Publication Data

US 2008/0040344 A1 Feb. 14, 2008

(51) Int. Cl.
G06F 17/30 (2006.01)
G06F 7/00 (2006.01)
(52) U.S. Cl. .............. 707/758; 702/1; 702/19; 706/54; 99/324; 73/865.7
(58) Field of Classification Search ................ None
See application file for complete search history.

(56) References Cited

U.S. PATENT DOCUMENTS

| 6,370,513 | B1* | 4/2002 | Kolawa et al. ................ 705/10 |
| 6,623,427 | B2* | 9/2003 | Mandigo ..................... 600/300 |
| 7,593,863 | B1* | 9/2009 | Sunshine et al. .............. 705/15 |
| 2003/0004937 | A1* | 1/2003 | Salmenkaita et al. ........... 707/3 |
| 2003/0060728 | A1 | 3/2003 | Mandigo |
| 2004/0107053 | A1* | 6/2004 | Pelletier ..................... 702/19 |

FOREIGN PATENT DOCUMENTS

JP 62-251659 11/1987

(Continued)

OTHER PUBLICATIONS

Connie Cheng and Leonard Bonanni, Counter Intelligence-MIT Media Lab, "Intelligent Spoon," website: http://www.media.mit.edu/ci/projects/intelligentspoon.html, Initial Date Unknown.*

(Continued)

Primary Examiner—Charles Rones
Assistant Examiner—Alicia M Lewis
(74) Attorney, Agent, or Firm—Day Pitney LLP

(57) ABSTRACT

There has been conventionally a problem that when the searcher uses, for example, "dry wine" selected according to the searcher's preference as a search key, the searcher cannot be satisfied with the search result because wine entries stored in a database as "dry wines" depend on objective evaluation by another person. A sense database is created by using, as a subjective search index, sense parameter information such as potential variation caused by pungency obtained by a pseudo sensor irrespective of one's ability. Specifically the database comprises a sense information obtaining section for obtaining sense information by associating the sense parameter information acquired by the sensor with representative information, a sense information storage section, a search key obtaining section, and a searching section for searching the sense information storage section using a search key.

2 Claims, 26 Drawing Sheets

FOREIGN PATENT DOCUMENTS

| | | |
|---|---|---|
| JP | 63-241354 | 10/1988 |
| JP | 63-297929 | 12/1988 |
| JP | 06-174689 | 6/1994 |
| JP | 7-103484 | 4/1995 |
| JP | 07-107924 | 4/1995 |
| JP | 07-204168 | 8/1995 |
| JP | 08-190573 | 7/1996 |
| JP | 11-328203 | 11/1999 |
| JP | 2002-117059 | 4/2002 |
| JP | 2003-331186 | 11/2003 |

OTHER PUBLICATIONS

Edmonds, Molly, "How Can My Spoon Taste My Food for Me?" Apr. 23, 2008, How Stuff Works, Inc., website: http://electronics.howstuffworks.com/gadgets/kitchen/spoon-taste-food1.htm.*

James Giese; "Electronic Noses", Food Technology, Mar. 2000, p. 96, vol. 54, No. 3, U.S.A.

Tsung Tan et al., "Electronic Tongue: A New Dimension in Sensory Analysis", Food Technology, Oct. 2001, p. 44, 46, 48, 50, vol. 55, No. 10, U.S.A.

Michael G. Madsen et al., "Spices, Flavor Systems, the Electronic Nose", Food Technology, Mar. 2000, p. 44-46, vol. 54, No. 3, U.S.A.

Toshikazu Kato, Sensory Database System, The Journal of the Institute of Image Information and Television Engineers, 1998, pp. 49-53, vol. 52, No. 1, Japan.

Haruo Kimoto, Kazuhiko Kushima, Hitoshi Shibagaki, Establishment of technology for image searching using sensitivity terms, NTT Technical Journal, 1998, 1D, Japan.

Kimoto et al., "Establishment of adjectives based image search technology—Search for images using keywords sensibility", R&D Report, NTT Technical Journal, Oct. 1, 1998, pp. 109-111, vol. 10 No. 10, The Telecommunications Association.

Toshikazu Kato, "3-2 Sensitivity Database System—Multimedia Database System in which Subjective Contents Search is Possible", ITE Journal, Jan. 20, 1998, pp. 49-52, vol. 52 No. 1, The Institute of Image Information and Television Engineers.

* cited by examiner

Fig. 3

Sensory information

○ × ramen

- Light-taste ramen

| 20 | 16 | 09 | 32 | 10 |

- Heavy-taste ramen

| 26 | 10 | 12 | 24 | 20 |

Fig 4

| Representative information1 | Representative information2 | Sensory parameter information | | | | | |
|---|---|---|---|---|---|---|---|
| ○×ramen | Heavy-taste ramen | 2 6 | 1 0 | 1 2 | 2 4 | 2 0 | |
| ○×ramen | Light-taste ramen | 2 0 | 1 6 | 0 9 | 3 2 | 1 0 | |
| Y-an Shinbashi shop | Soy sauce-based ramen | 1 6 | 2 4 | 2 0 | 1 6 | 3 2 | |
| ⋮ | ⋮ | ⋮ | | | | | |

Fig 18

| Representative information1 | Representative information2 | Representative information3 | Sensory parameter information | | | | |
|---|---|---|---|---|---|---|---|
| ○× ramen | Salt-based ramen | Light-taste | 16 | 20 | 12 | 09 | 15 |
| ○× ramen | Pork and soy sauce-based ramen | Heavy-taste | 24 | 10 | 09 | 32 | 20 |
| Y-an Shinbashi shop | Hell ramen | Super hot | 12 | 14 | 31 | 34 | 10 |
| ⋮ | ⋮ | ⋮ | ⋮ | | | | |

Fig. 21

|  | Stress | Delight | Sorrow | Relax |
|---|---|---|---|---|
| Comedy duo B | 4 | 6 | 2 | 2 |
| ⋮ |  |  |  |  |
| Movie C | 2 | 4 | 5 | 2 |
| ⋮ | ⋮ | ⋮ | ⋮ | ⋮ |

Fig. 24
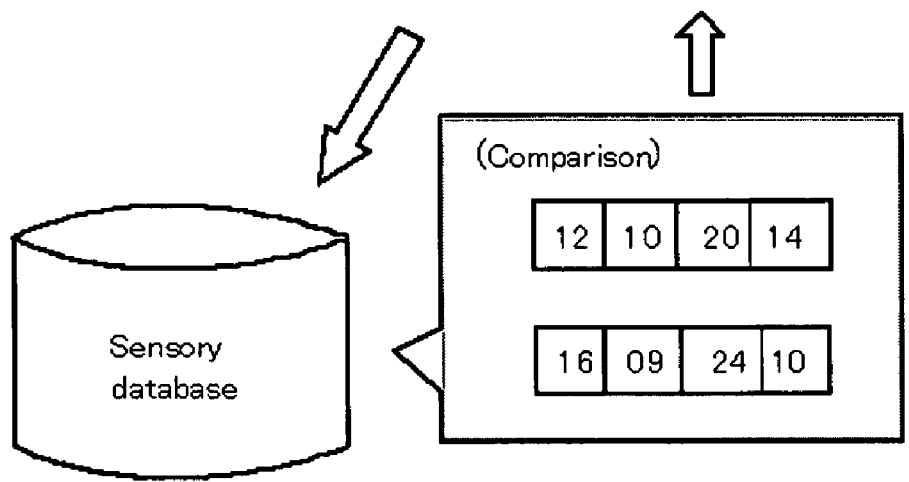
<Advice information of adjustment of taste>
- Add 4g of salt
- Add 5g of sugar

SENSE DATABASE

BACKGROUND OF THE INVENTION

1. Field of the Invention

The present invention relates to a technology for storing and searching for information objectively indicating parameters of five senses or emotions etc. arisen in people from objects.

2. Description of the Related Art

Recently, by means of a database storing a variety of information, a user can search for and acquire the desired information. In Japanese Patent Publication No. 2003-331186, a technology relating to a database of wine is disclosed. Specifically, the technology is for a user to search for the wine he desires by means of the database, in which the producer's information such as wine brand and additional information such as rating of taste are correlated and stored.

However, the rating of taste etc. stored in the database is evaluated by a person such as a producer, so it is a subjective evaluation depending on personal quality or sensitivity etc. Therefore, for example, the wine A, which has been searched and acquired as a 'dry wine' by a user, may possibly to be not dry at all to the user. This possibly happens even if a sommelier, certified as a person with specialized knowledge about wine by the third party, becomes the rater.

In Japanese Patent Publication No. 2002-117059, the database, which can be searched based on the more objective information, and the search apparatus thereof have been disclosed. In Japanese Patent Publication No. 2002-117059, as examples of the objective information, ingredients, process, production area, and age etc. of wine are cited. Actually, it is known that the taste of wine largely depends on these objective data. For example, a price of a wine is set depending on the data such as 'an 80-year-old wine produced by chateau B'. Further, in Japanese Patent Publication No. 2002-117059, it is described that if tactile sense is emphasized, material, structure, and shape etc. of the object are used as the objective data, and if visual sense is emphasized, color and texture etc. are used as the objective data. Then, for example, it becomes possible for a user to search for a wine, of which production area and age are the same or similar to the wine known by the user, by setting the wine known by the user to the search key. Further, for example, it becomes possible for a user to search for a painting, of which production color and texture are the same or similar to the painting known by the user, by setting the painting known by the user to the search key.

However, even in Japanese Patent Publication No. 2002-117059, the subjective factor affects the search result. The reason for this is that, in cases where the user makes subjective judgment that they are different, the search result is regarded as being incorrect, even in the case of a wine having similarity in production area or age etc., or even in the case of a movie having similarity in rendition of color, story, cast etc.

Accordingly, similarly to the case where the first Qin Emperor unified the units of weights and measures, thereby enabling measurement by unified standards, it is necessary to establish the unified standards in search, thereby providing a database and a system, in which the search result, unaffected by personal quality or sensitivity, can be acquired.

SUMMARY OF THE INVENTION

In order to solve the above deficiencies, the present invention provides a database, in which, for example, physiological change such as change in electrical potential caused by taste such as sweet taste or flavor of wine is acquired through simulation by means of a sensor imitating a human sensory organ, and the physiological change is used as an objective indication. Thus, by means of the mechanical sensor imitating human sensory organ, it becomes possible to acquire extremely objective data unaffected by personal quality or the nervous system.

Alternatively, for example, the sensory database, in which change of brain waves or production of brain chemicals etc. caused by entertainment is measured by a machine, and amusingness, thrill, or excitement of the entertainment are indicated, thereby carrying out search, is provided.

The present invention is, specifically, a sensory database, comprising, an acquirer for sensory information, which acquires sensory information, in which sensory parameter information indicating sense acquired by a sensor and representative information representing the sense are correlated, a storage for sensory information, which stores the sensory information acquired by said acquirer for sensory information, an acquirer for search key, which acquires the representative information as a search key, and a searcher, which searches said storage for sensory information based on the search key acquired by said acquirer for search key.

According to the present invention of the above configuration, it becomes possible to carry out a search, for example, based on the information indicating change of electrical potential in the mechanically imitated taste cell caused by a certain meal, or on the information indicating production of endorphin or change of α-wave caused by watching a certain movie. Accordingly, by means of this sensory parameter information, an objective indication, for example, it becomes possible to search for a meal, of which change of electrical potential is equal to that of the meal eaten by the user.

Consequently, for example, change of electrical potential (physiological change), equal to that caused by a previously eaten meal, is caused by the searched meal, thereby getting equal satisfaction.

Thus, similarly to the case where the units of weight and measure are unified, thereby enabling determination based on measurement results by means of unified standards, it becomes possible to carry out a search by means of the objective search standards mechanically simulated.

BRIEF DESCRIPTION OF THE DRAWINGS

FIG. 3 is a pattern diagram exemplifying the sensory parameter information of the first embodiment;

FIG. 4 is a pattern diagram exemplifying the sensory information stored in the storage for sensory information of the first embodiment;

FIG. 18 is a diagram exemplifying the representative information of the sixth embodiment;

FIG. 21 is a diagram exemplifying the emotional vector computed from the electroencephalogram measured by the brain sensor of the ninth embodiment;

FIG. 24 is a pattern diagram exemplifying the acquisition of the advice information of adjustment of taste by the acquirer for advice information of adjustment of taste of the tenth embodiment;

DETAILED DESCRIPTION OF THE PREFERRED EMBODIMENTS

Embodiments of the present invention will be described hereinbelow with reference to the drawings. The present invention is not to be limited to the above embodiments and able to be embodied in various forms without departing from the scope thereof.

Figure 1:
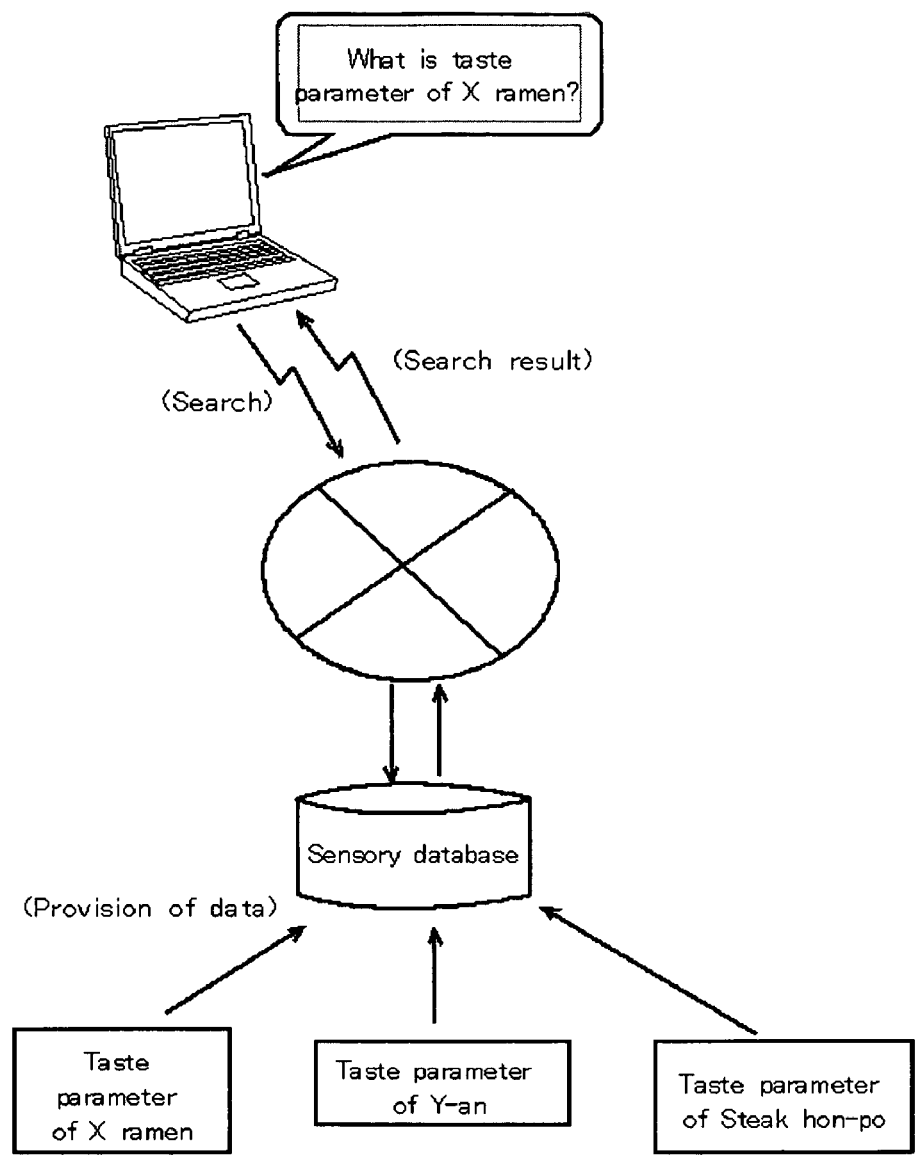
FIG. 1 is a diagram exemplifying a scheme of the search by means of the sensory database of the first embodiment.

FIG. 1 is a diagram exemplifying a scheme of the search by means of the sensory database of the first embodiment. As shown in FIG. 1, at the outset, the taste parameters of respective menus of 'X ramen shop', 'Y-an', or 'Steak hon-po' etc., are stored in the sensory database. Note that, the taste parameter is a parameter indicating taste such as 'sweet taste' or 'flavor' indicated by change of electrical potential, which is objective and unaffected by personal quality or sensitivity etc. acquired by the taste sensor, a device described hereinbelow.

Here, a user tries to cook by reproducing taste of X ramen shop. He accesses the sensory database by means of a personal computer connected to the internet, and inputs 'X ramen shop' as the search key to the browser. Then, the sensory database searches for and acquires the taste parameter by the search key as an argument. After that, the acquired taste parameter of X ramen shop is returned to the user's personal computer as a search result.

Thus, by means of the sensory database of the first embodiment, for example, it becomes possible to acquire the information indicating taste etc. as an objective parameter. Therefore, by means of this parameter indicating sense as a clue, it becomes possible to reproduce a similar meal, or to carry out a search for another restaurant, which provides a meal of similar taste using the sensory database again.

Note that, the sensory database of the first embodiment is not limited to the taste parameter as described above, and may be the sensory database, in which the pain parameter indicating change of electric potential caused by pain is correlated with a dentist, or the sensory database, in which the amusement parameter of the entertainment product such as a movie indicated by the production of endorphin or the amount of $\alpha$-wave is stored and used for searching.

Figure 2:
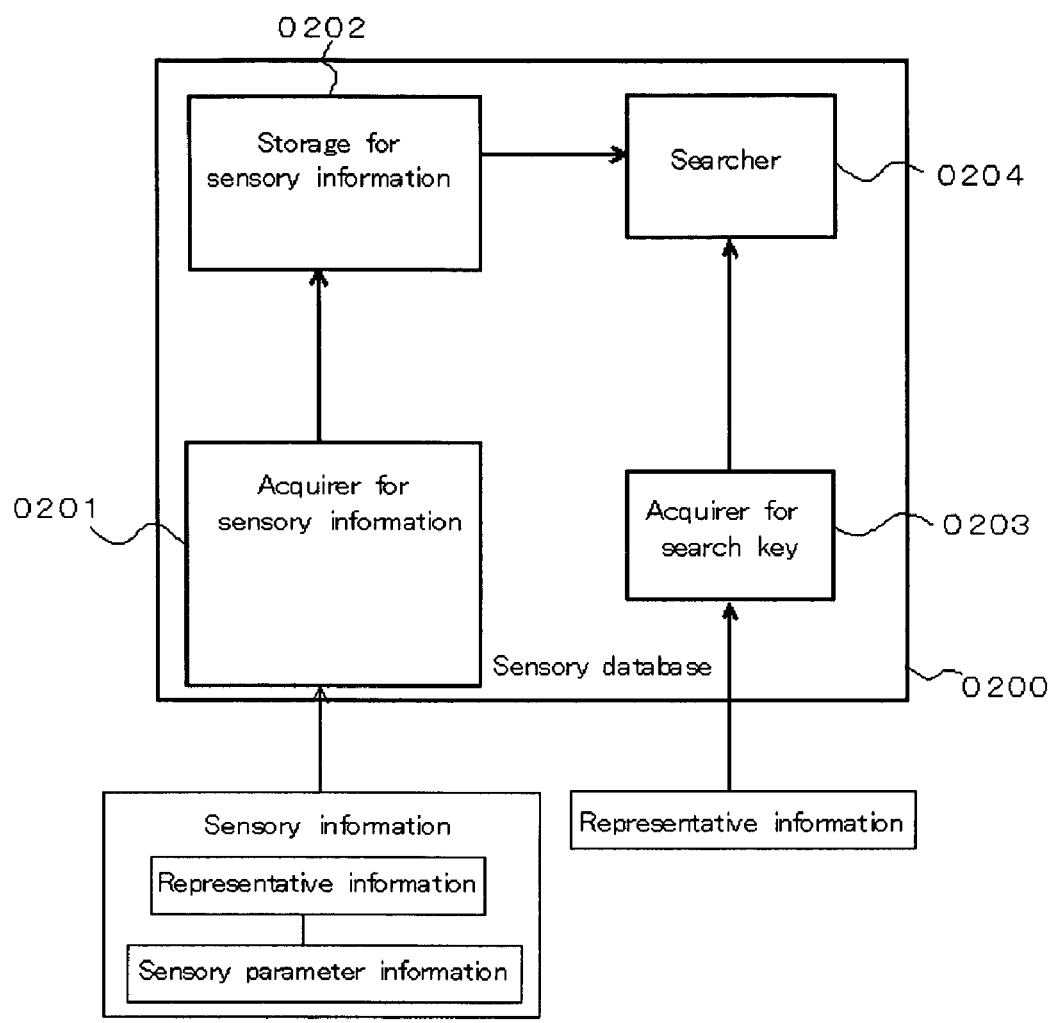
FIG. 2 is a functional block diagram of the sensory database of the first embodiment.

FIG. 2 is a functional block diagram of the sensory database of the first embodiment. As shown in FIG. 2, the 'sensory database' (0200) of the first embodiment comprises the 'acquirer for sensory information' (0201), the 'storage for sensory information' (0202), the 'acquirer for search key' (0203), and the 'searcher' (0204).

Note that, the functional block of respective apparatuses described hereinbelow can be implemented as a hardware, a software, or both hardware and software. Specifically, by means of computer, CPU, memory, bus, hard-disk drive, reading driver such as CD-ROM, or DVD-ROM, transmission/reception port for various communications, interface, hardware component such as other peripheral devices, and driver program for controlling the hardware, and other application programs.

Specifically, by sequentially executing programs on the memory, the data on the memory and the data inputted via the interface are processed, stored, and outputted etc., thereby implementing functions of respective units.

Further, the present invention can be implemented not only as apparatus or system, but also as method thereof. Further, a portion of such invention may be configured as software. Furthermore, a software product used for causing a computer to execute the software, and the recording medium, in which the software is installed, should be included in the technical scope of the present invention (the same is applied through the entire specification).

The 'acquirer for sensory information' (0201) acquires the sensory information, in which the sensory parameter information is correlated with the representative information. The 'sensory parameter information' is a parameter indicating sense acquired by a sensor. Examples of the 'sensor' include the taste sensor, in which change of electric potential caused by stimulus applied to taste cell by taste substance is mechanically simulated and measured, the olfactory sensor, in which change of electric potential caused by stimulus applied to smell cell by smell substance is mechanically simulated and measured, and the brain sensor, in which production of endorphin, brain substance, and brain waves such as $\alpha$-waves or $\beta$-wave are mechanically measured.

Note that, an example of the taste sensor is particularly disclosed in Japanese Patent No. 2578370. The technology is for making an artificial tongue by means of a model of imitation of the tongue. Specifically, in the technology, multiple lipid polymer membranes, an imitation of the biological film of taste cells in the tongue, are caused to receive taste substance, thereby detecting and measuring changes in electric potential. By means of such a taste sensor, it becomes possible to detect a synergistic effect (e.g., a watermelon with salt tastes sweet), or a suppressive effect (e.g., coffee with sugar tastes less bitter), which cannot be measured by constituent amount of taste alone. Thus, by means of the taste sensor configured by mechanically imitating the human body, it becomes possible to objectively measure without being influenced by the personal quality or sense of taste.

FIG. 3 is a pattern diagram exemplifying the sensory parameter information of the first embodiment. In FIG. 3, numbers exemplify the sensory parameter information acquired by the sensor. An example of the sensory parameter information includes numerical values, which indicate strength and weakness of five elements of taste such as bitterness, sweetness, acidity, and saltiness, digitalized by the taste sensor. Thus, by means of the objective numerical value indicating change of electric potential acquired by the taste sensor, it becomes possible to express taste.

In addition, as for the other sensors of five senses, the 'irritant receptor', the 'converter for electric signal', the 'transmission of signal', and the 'detection of signal' have the same the process. For example, in the case of a visual sensor, a photoelectric converter, converting received light to an electric signal, may be used. Further, in the case of the olfactory sensor, cantilever array coated with different types of polymers as receptor of smell substance may be used.

Similarly, the brain sensor is disclosed in Japanese Patent Publication No. H7-204168. This is the method, in which a cross-correlation function for three brain waves ($\theta$-wave, $\alpha$-wave, and $\beta$-wave) and the parameter as state vector are acquired, so that an emotional vector indicating four emotions (delight, anger, sorrow and pleasure) are computed by means of linear conversion.

The 'representative information' is the information representing sense indicated by the parameter. In the case of the sensory parameter information of taste, an example of the representative information including name of the meal, name of the cook, name of the restaurant, and the area name, which have the above parameter, or qualitative evaluation information for taste such as 'tasty', 'heavy-taste', or 'super-hot'. Further, in the case of the sensory parameter information of risibility, an example of the representative information include name of the movie, name of the director, cast, or qualitative information such as 'extremely funny', or 'intellectually funny'.

FIG. 3 is a pattern diagram exemplifying the sensory information, in which the representative information and the sensory parameter information are correlated. As shown in this diagram, in the sensory information, the representative information such as 'X ramen shop', the name of restaurant, 'light-taste ramen' and 'heavy-taste ramen', the name of meal, and the sensory parameter information, which is the objectively measured information acquired by the taste sensor, such as 'bitter taste: 20, sweet taste: 16, acidic taste: 09, flavor: 32, and salty taste: 10' or 'bitter taste: 26, sweet taste: 10, acidic taste: 12, flavor: 24, and salty taste: 20' are correlated.

Thus, for example, the name of the restaurant or meal, and the sensory parameter information objectively indicating the taste of the meal are correlated and stored, so that it becomes possible for a user to carry out a search for a restaurant providing a meal of desired taste based on the objective indicator uninfluenced by personal quality or sense.

Further, as to the sensory information, the representative information such as name of film, name of director, cast, and producer, and the sensory parameter information such as 'delight: 5, anger: 1, sorrow: 3, and pleasure: 7' may be correlated. Further, as to the sensory information, the information indicating an effect of aroma such as 'relax' as the representative information, and the information indicating formulation of smell having the effect such as 'chamomile: 5, sandalwood: 4, and marjoram: 1' as the sensory parameter information objectively measured by the olfactory sensor may be correlated and stored. Further, as the sensory information, the representative information such as name of the dentist, and the information of objective pain level based on the strength and weakness of the electric signal caused by the pain such as 'pain level: 8/10' as the sensory parameter information objectively measured by the tactile sensor may be correlated.

The 'storage for sensory information' (0202) stores the sensory information acquired by the 'acquirer for sensory information' (0201).

FIG. 4 is a pattern diagram exemplifying the sensory information stored in the storage for sensory information. As shown in this diagram, the representative information such as 'heavy-taste ramen' of 'X ramen shop' and the sensory parameter information such as '26, 10, 12, 24, and 20' are correlated and stored.

Note that this storage may be carried out in the form of relational database, expressing one data as a set of multiple items in order to improve search speed.

The 'acquirer for search key' (0203) acquires the representative information as the search key. Therefore, the representative information such as 'X ramen shop' or 'super-hot' is acquired, and a search for a restaurant correlated with the sensory parameter information, or a search for a restaurant, offering a similar taste to the 'X ramen shop', therefore, a restaurant correlated with sensory parameter information similar to the above sensory parameter information is carried out.

Figure 5:
FIG. 5 is a diagram exemplifying the Web page for acquiring the representative information by means of the sensory database of the first embodiment.

FIG. 5 is a diagram exemplifying the Web page for acquiring the representative information. Thus, in the many case, the sensory database of the first embodiment is set on the internet, and the screen shown in FIG. 5 is displayed on a client terminal via the internet according to the request from the client terminal. Then, the inputted representative information is acquired via the internet line, and the search is carried out. Of course, this is just one of the embodiments, and the application of the present invention is not limited to the internet.

As shown in FIG. 5, in the case of the sensory database of taste, the Web page for searching for a restaurant, of which offers a similar taste to a certain restaurant, is displayed on the client terminal, which sent a request. The user who inputted the restaurant name from the client terminal, specifies the area, and requests a search for a ramen shop providing a ramen having a taste similar to the ramen having the taste desired by the user. Then, by means of the representative information and area information desired by the user, which are used as an argument, the search is carried out by the searcher described hereinbelow, so that the name of restaurant and the access route to the restaurant are displayed.

The 'searcher' (0204) searches the storage for sensory information (0202) based on the search key acquired by the acquirer for search key (0203). As described above, by means of the representative information as an argument, for example, the sensory parameter information of the heavy-taste ramen of the X ramen shop is searched for.

In addition, as shown in FIG. 5, in order to search for a restaurant having similar taste, by means of the representative information as the search key, the representative information may be returned to the user. In this case, based on the representative information acquired by the acquirer for search key, the sensory parameter information is acquired. Then, the sensory parameter information, which has the value fulfilling a condition that, for example, more than two values are the same and the difference between the two values is less than 1, is searched for. Subsequently, the representative information such as name of restaurant, correlated with the searched sensory parameter information, is searched for and outputted to the user's terminal as the search result.

Of course, the information, which is searched for by the searcher by means of the representative information as the search key and is outputted as the search result to the user's terminal, may be other than the sensory parameter information or the representative information as the sensory information. Therefore, other information correlated with the sensory information such as the information indicating number of seats in the restaurant having a similar taste or the information indicating average waiting time may be used.

Thus, according to the sensory database of the first embodiment, it becomes possible to carry out search based on the sensory parameter information objectively measured by the sensor, thereby enabling a search for things such as a restaurant of similar taste or a film having the same amusingness, which have been difficult to be searched in the conventional search method.

Alternatively, it becomes possible to carry out searching for things difficult to be searched satisfactorily.

Figure 6:
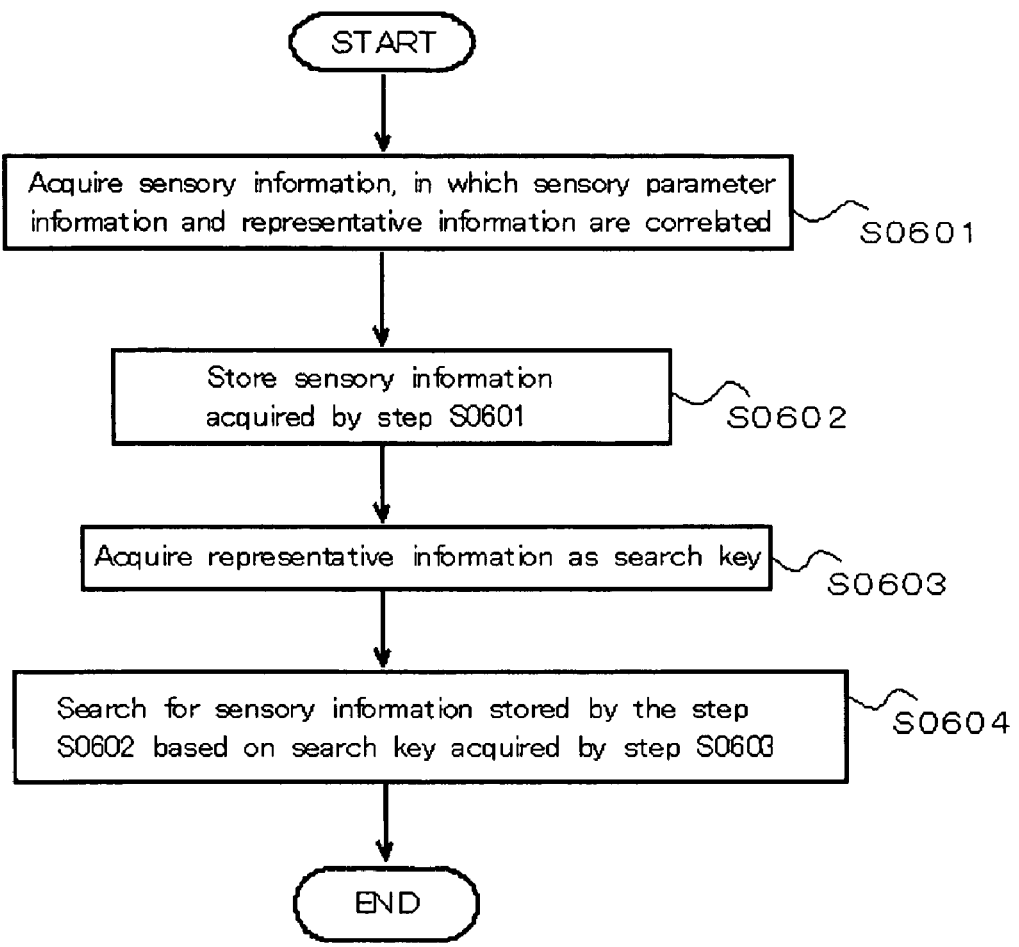
FIG. 6 is a flow chart showing the processing flow of the first embodiment.

FIG. 6 is a flow chart showing the processing flow of the first embodiment. The processing flow of the first embodiment is as follows. At the outset, the sensory information, the sensory parameter information and the representative information are correlated (step S0601). Subsequently, the sensory information acquired by said step S0601 is stored (step S0602). Then, the representative information is acquired as the search key (step S0603). Finally, the sensory information stored by said step S0602 is searched for based on the search key acquired by said step S0603 (step S0604).

Figure 26:
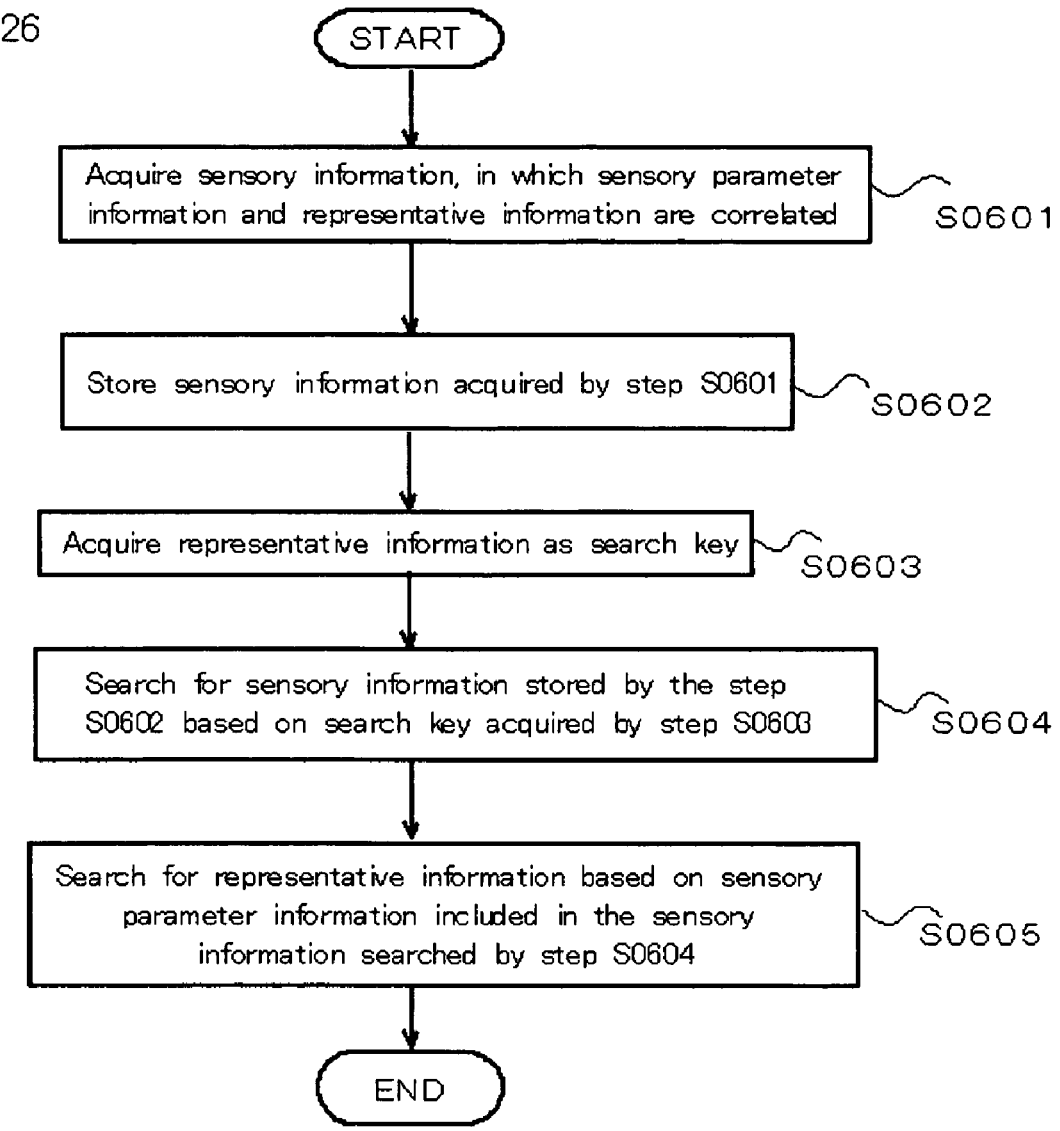
FIG. 26 is a flow chart showing another processing flow of the first embodiment.

As shown in FIG. 26, the other representative information may be acquired based on the sensory parameter information included in the sensory information searched by step S0604 (step S0605). Thus, for example, it becomes possible to search for the representative information such as name of the restaurant having the sensory parameter information of taste, which has a similar taste to the taste of the restaurant as the search key.

As described above, according to the sensory database of the first embodiment, it becomes possible to carry out a search based on the sensory parameter information objectively measured by the sensor, thereby enabling a search for a thing such as a restaurant having a similar taste or a film having the same amusingness, which have been difficult to be searched for in conventional search methods, or to carry out searches for things difficult to be satisfactorily searched for.

Figure 7:
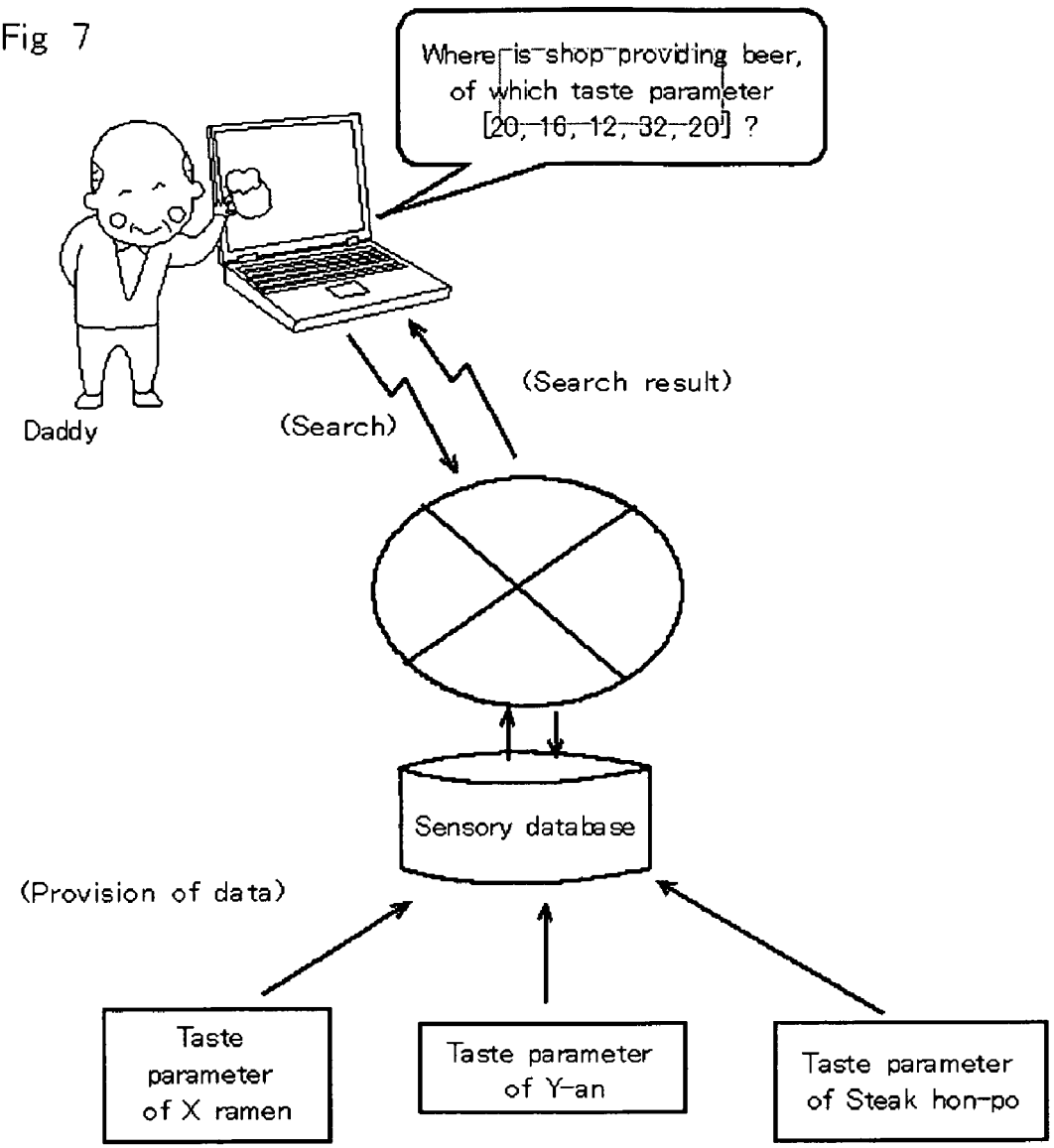
FIG. 7 is a diagram exemplifying a scheme of the search by means of the sensory database of the second embodiment.

FIG. 7 is a diagram exemplifying a scheme of the search by means of the sensory database of the second embodiment. As shown in this diagram, the second embodiment is search for by means of the sensory database similarly to the first embodiment. The difference is that the sensory parameter information, not the representative information, is used as the search key. For example, in cases where a family owns a handy-type taste sensor, and they measure the sensory parameter information of a tasty local beer drunk at home, father of the family, who wants to drink an other beer having a taste similar to the beer drunk at home, carries out a search using the sensory parameter information as the search key, so that he can search for the beer having a similar taste.

Figure 8:
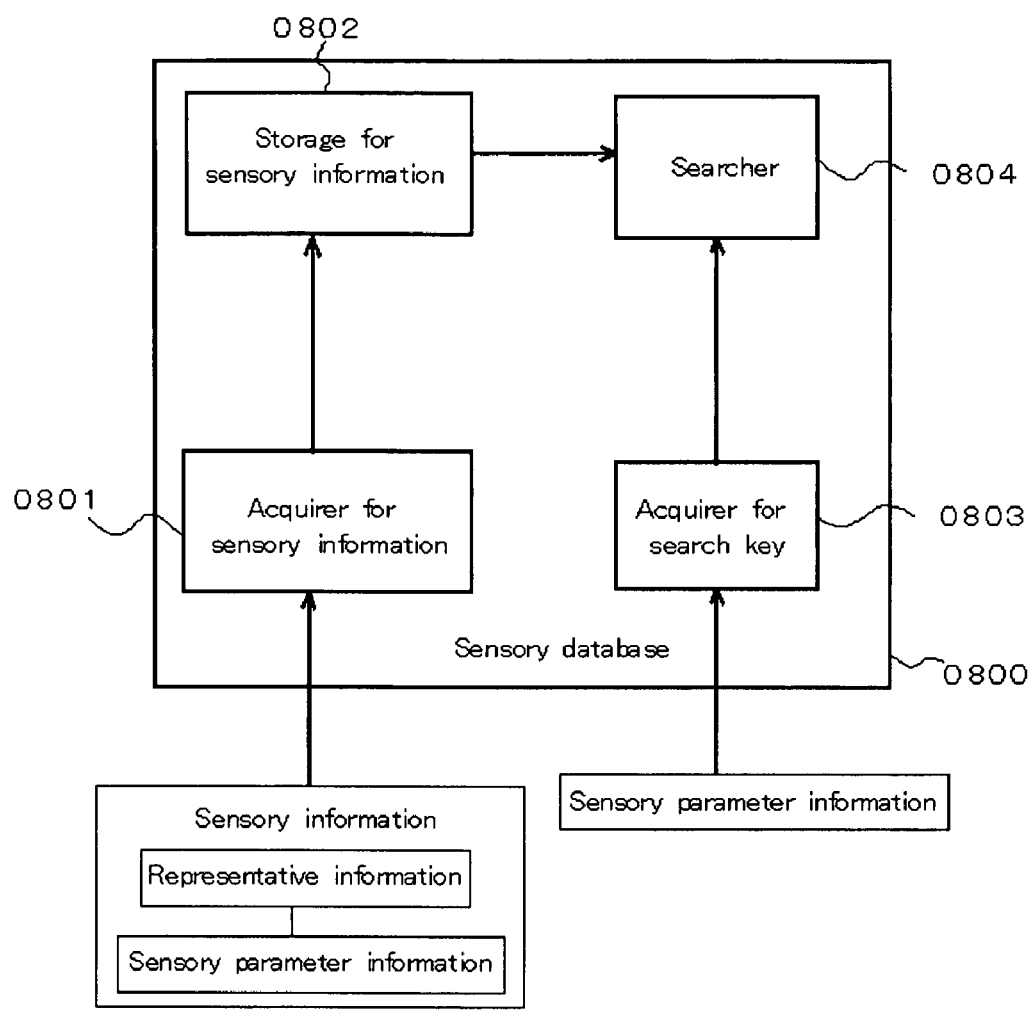
FIG. 8 is a functional block diagram of the sensory database of the second embodiment.

FIG. 8 is a functional block diagram of the sensory database of the second embodiment. As shown in FIG. 8, the 'sensory database' (0800) of the second embodiment comprises the 'acquirer for sensory information' (0801), the 'storage for sensory information' (0802), the 'acquirer for search key' (0803), and the 'searcher' (0804).

Thus, the sensory database of the second embodiment is characterized in that the sensory parameter information, not the representative information, is used as the search key by the 'acquirer for search key' (0803), and the 'searcher' (0804) carries out search by means of the sensory parameter information as the search key. In addition to the above case where the search object is the representative information, the search object may be the sensory parameter information. Therefore, for example, by means of the sensory parameter information as the search key, the sensory parameter information of similar taste may be searched for.

Note that, the 'acquirer for sensory information' (0801), the 'storage for sensory information' (0802) are the same as those of the first embodiment, so that the description thereof will be omitted.

Figure 9:
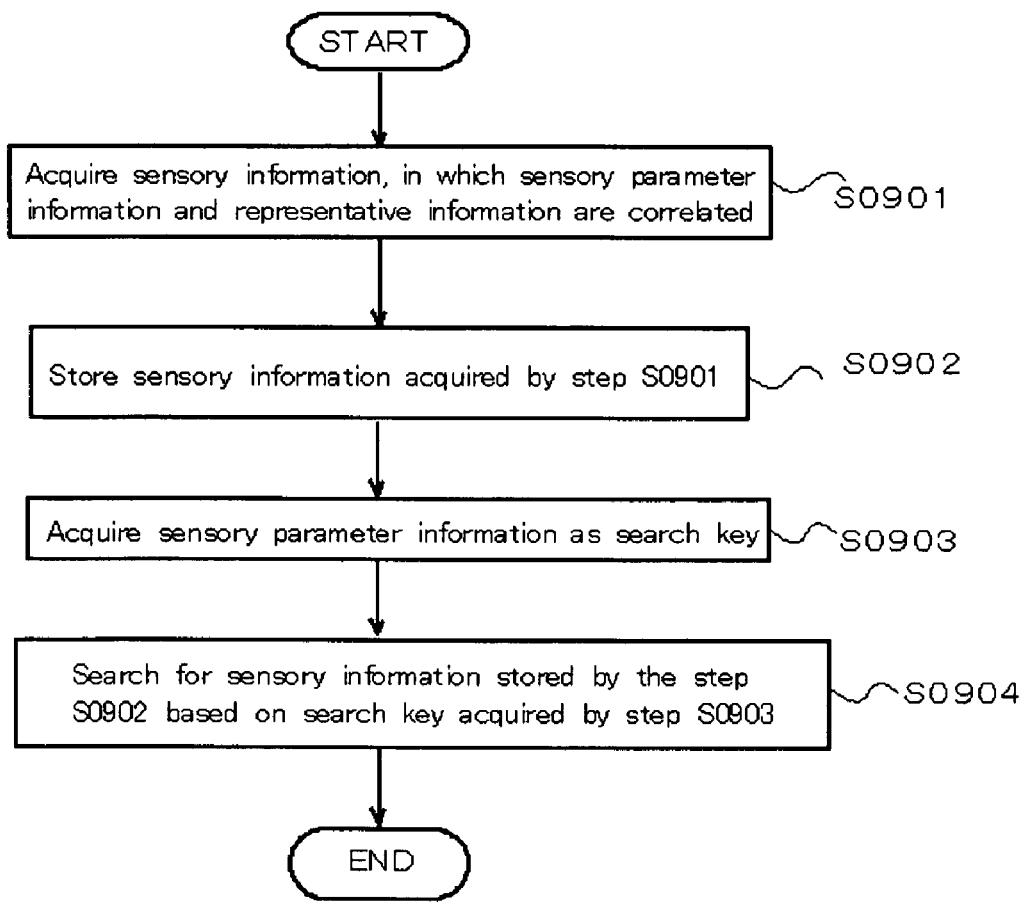
FIG. 9 is a flow chart showing the processing flow of the second embodiment.

FIG. 9 is a flow chart showing the processing flow of the second embodiment. The processing flow of the second embodiment is as follows. At the outset, the sensory information, in which the sensory parameter information and the representative information are correlated (step S0901). Subsequently, the sensory information acquired by said step S0901 is stored (step S0902). Then, the sensory parameter information is acquired as the search key (step S0903). Finally, the sensory information stored by said step S0902 is searched based on the search key acquired by said step S0903 (step S0904).

As described above, according to the sensory database of the second embodiment, similarly to the first embodiment, it becomes possible to carry out a search based on the sensory parameter information objectively measured by the sensor. In addition, it becomes possible to carry out search, for example, in the case where the sensory parameter information of taste is known, but it is unknown which restaurant has the sensory parameter information.

Figure 10:
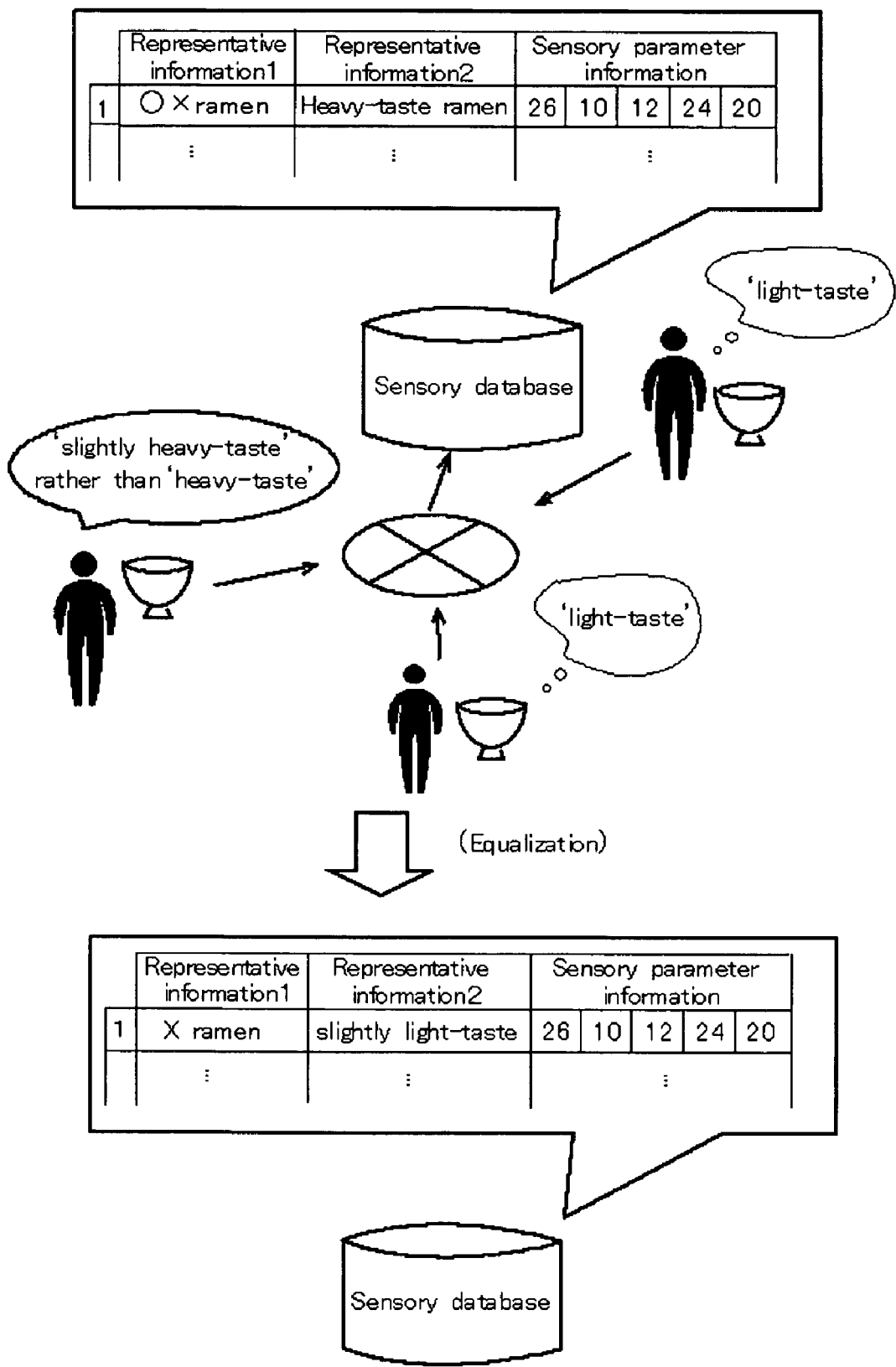
FIG. 10 is a diagram exemplifying a scheme of the sensory database of the third embodiment.

FIG. 10 is a diagram exemplifying a scheme of the sensory database of the third embodiment. As shown in this diagram, in the sensory database of the third embodiment, the representative information such as 'X ramen', name of the meal, or 'heavy-taste', evaluation of taste of the X ramen, are correlated with the sensory parameter information, and stored. Here, people, who ate the X ramen, have different feeling of taste such as 'slightly heavy-taste', or 'light-taste'. Then, the people send the respective feelings to the sensory database via the internet etc. Then, in the sensory database, the received feelings are statistically processed. Here, for example, if there are many feelings as 'light-taste', this feeling is statistically processed and equalized, so that the feeling of taste as the representative information is changed from 'heavy-taste' to 'light-taste'.

Thus, as to the representative information such as evaluation, by means of the internet etc., the information from many users is corrected, statistically processed, and equalized, so that it becomes possible to acquire the objective information not only as to the sensory parameter information but also as to the representative information. Note that the representative information, the object of the statistical processing, is not the information such as name of restaurant, which is not able to be statistically processed, and limited to the representative information, which is comparable and can be digitalized according to the nature of information such as evaluation information indicating 'tasty' or 'amusing' etc.

In addition, by applying the equalized representative information to the other representative information having the similar sensory parameter information, the entire sensory database may be equalized and the representative information may be objectivized.

Figure 11:
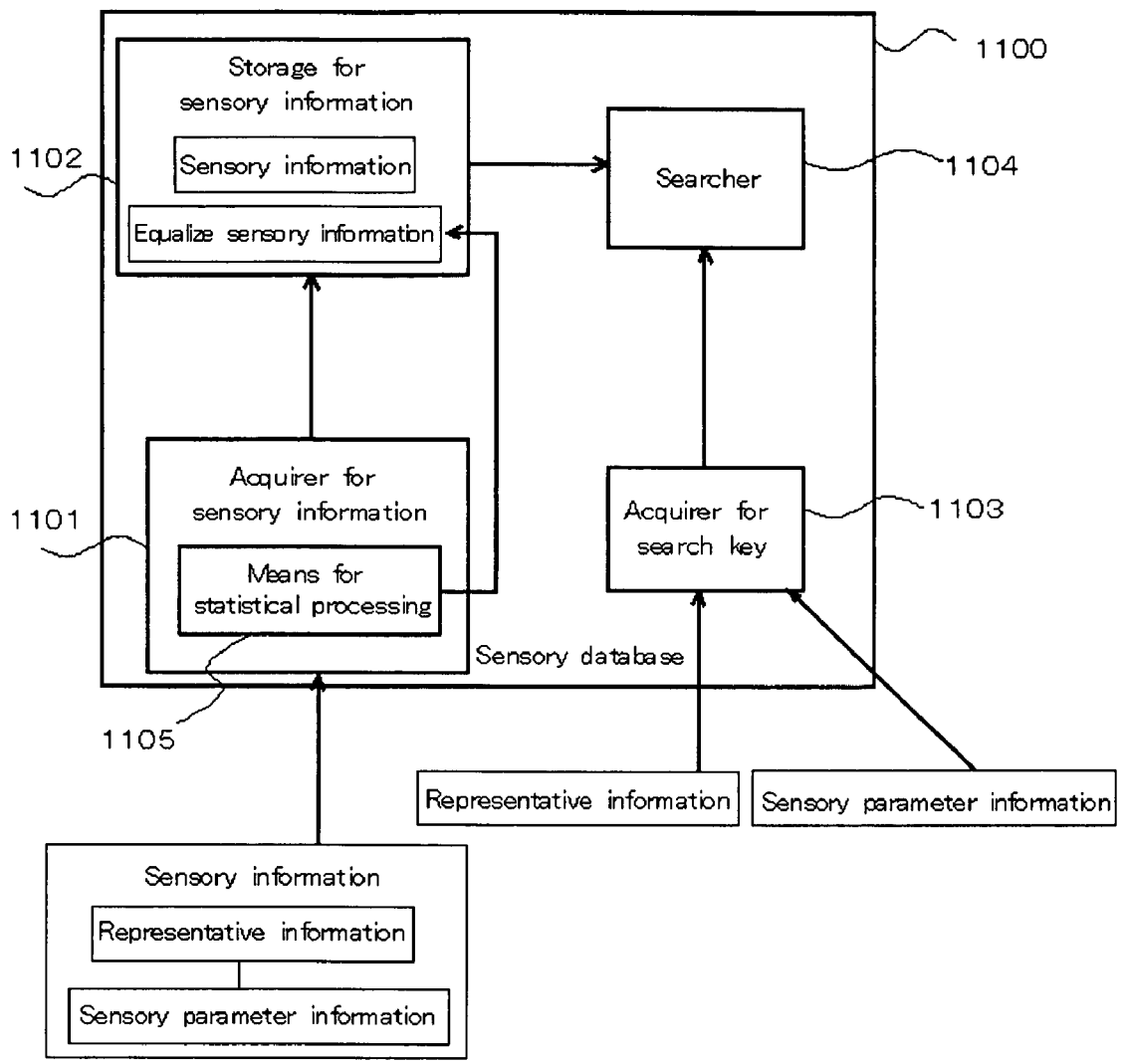
FIG. 11 is a functional block diagram of the sensory database of the third embodiment.

FIG. 11 is a functional block diagram of the sensory database of the third embodiment. As shown in FIG. 11, based on the first or second embodiment, the 'sensory database' (1100)

of the third embodiment comprises the 'acquirer for sensory information' (1101), the 'storage for sensory information' (1102), the 'acquirer for search key' (1103), and the 'searcher' (1104).

In addition, the sensory database of the third embodiment is characterized in that the acquirer for sensory information (1101) comprises the 'means for statistical processing' (1105). Note that, the 'acquirer for sensory information', the 'acquirer for search key', and the 'searcher' are the same as those of the first or second embodiment, so that the description thereof will be omitted.

The 'means for statistical processing' (1105) carries out statistical processing of the acquired sensory information, and equalizes the representative information correlated with a specific parameter. The term 'equalize' corresponds to a method for equalization by means of an average of digitalized representative information. Alternatively, standard deviation or normal distribution may be used. Further, the evaluation information such as 'tasty' may be equalized by preliminarily setting the evaluated value of it as described with reference to FIG. 12.

Figure 12:
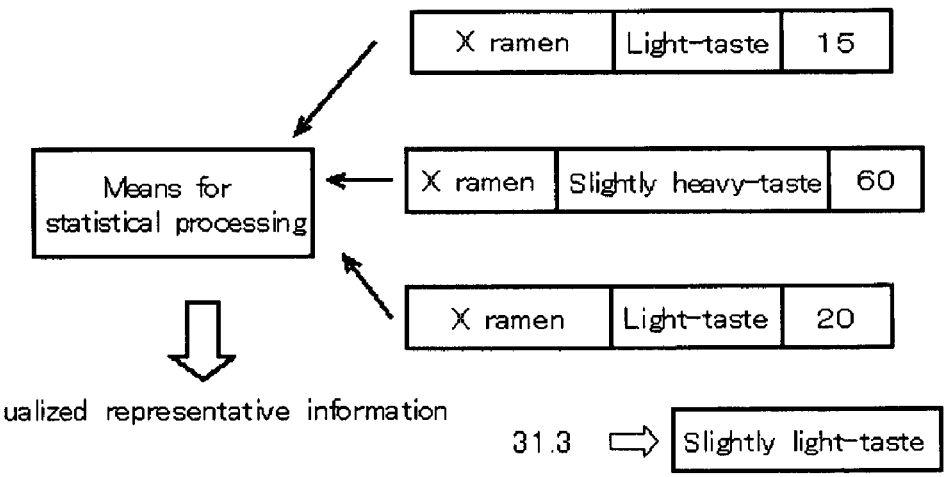
FIG. 12 is a diagram exemplifying a statistical processing of the means for statistical processing of the third embodiment.

FIG. 12 is a diagram exemplifying a statistical processing. As shown in this diagram, the representative information to be statistically processed is the information as to evaluation of taste, and the evaluated value is set for respective evaluations of taste. Specifically, the evaluated value of 'light-taste' is '0 to 20', the evaluated value of 'slightly light-taste' is '21 to 40', and the evaluated value of 'slightly heavy-taste' is '41 to 60'. Here, as to the evaluation of taste of the X ramen, three users sent the sensory information such as 'light-taste (the evaluated value: 15)', 'slightly heavy-taste (the evaluated value: 60)', and 'light-taste (the evaluated value: 20)', respectively. Then, in the sensory database, the means for statistical processing computes the average of the evaluated value '31.3'. This evaluated value corresponds to 'slightly light-taste', so that as to evaluation of taste as the representative information, the 'slightly light-taste', which has been equalized by the means for statistical processing, is acquired in the sensory database.

Thus, the representative information is statistically processed and equalized, thereby improving the accuracy of the representative information. Therefore, the representative information, which corresponds to more users and is generalized, can be acquired.

The storage for sensory information (1102) stores and manages equalized sensory information. The term 'equalized sensory information' is information in which the representative information equalized by the means for statistical processing (1105) and the specific parameter are correlated. Note that, the terms 'store and manage' may be implemented by updating the representative information indicating 'heavy-taste' to the equalized representative information indicating 'slightly light-taste', and storing it, or by storing them respectively and correlating both representative information with the sensory parameter information. Further, as described above, similarly, the representative information indicating the evaluation of taste of other ramen having similar taste parameter may be updated to the equalized representative information.

Thus, by storing and using the equalized sensory information for a search, in the case where the equalized sensory information is used as a search key, it becomes possible to search with satisfactory accuracy.

Figure 13:
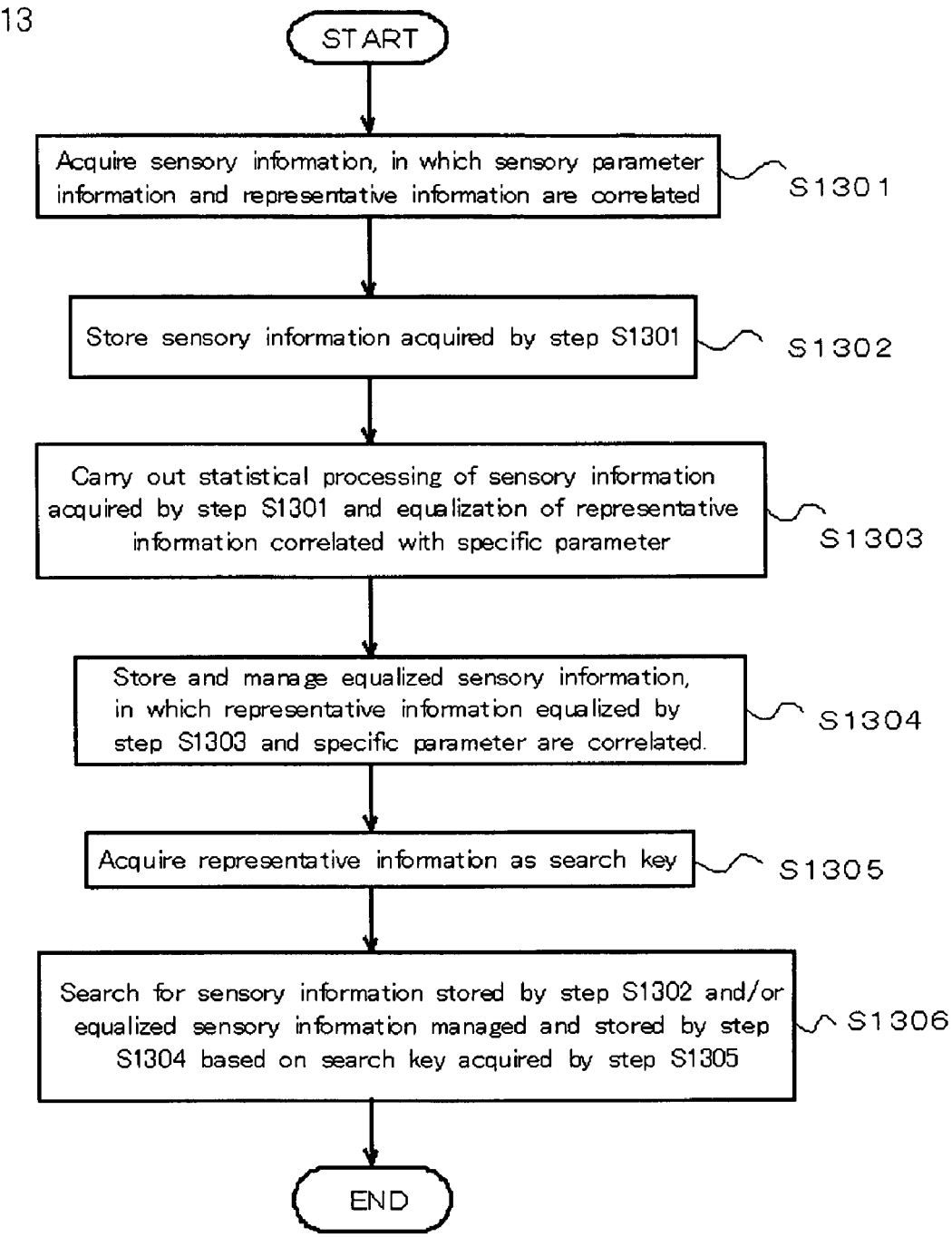
FIG. 13 is a flow chart showing the processing flow of the third embodiment.

FIG. 13 is a flow chart showing the processing flow of the third embodiment. The processing flow of the third embodiment is as follows. At the outset, the sensory information, in which the sensory parameter information and the representative information are correlated (step S1301). Subsequently, the sensory information acquired by said step S1301 is stored (step S1302). Then, the sensory information acquired by the step S1301 is statistically processed and the representative information correlated with a specific parameter is equalized (step S1303). Subsequently, the equalized sensory information, in which the representative information equalized by step S1303 and said specific parameter are correlated, is stored and managed (step S1304). Then, the representative information is acquired as the search key (step S1305). Finally, the sensory information stored by said step S1302, and/or the equalized sensory information managed and stored by step 1304 are searched for based on the search key acquired by said step S1305 (step S1306).

Note that the equalization process in step S1303 is not limited to the process for the sensory information acquired by step S1301. For example, the process may be for the sensory information, which is separately acquired after the sensory information acquired by step S1301 has been stored by step S1302. Further, the search key acquired by step S1305 may be the sensory information.

As described above, according to the sensory database of the third embodiment, the representative information is equalized, so that the representative information, which corresponds to more users and is generalized, can be acquired. Consequently, it becomes possible to search with satisfactory accuracy.

Figure 14:
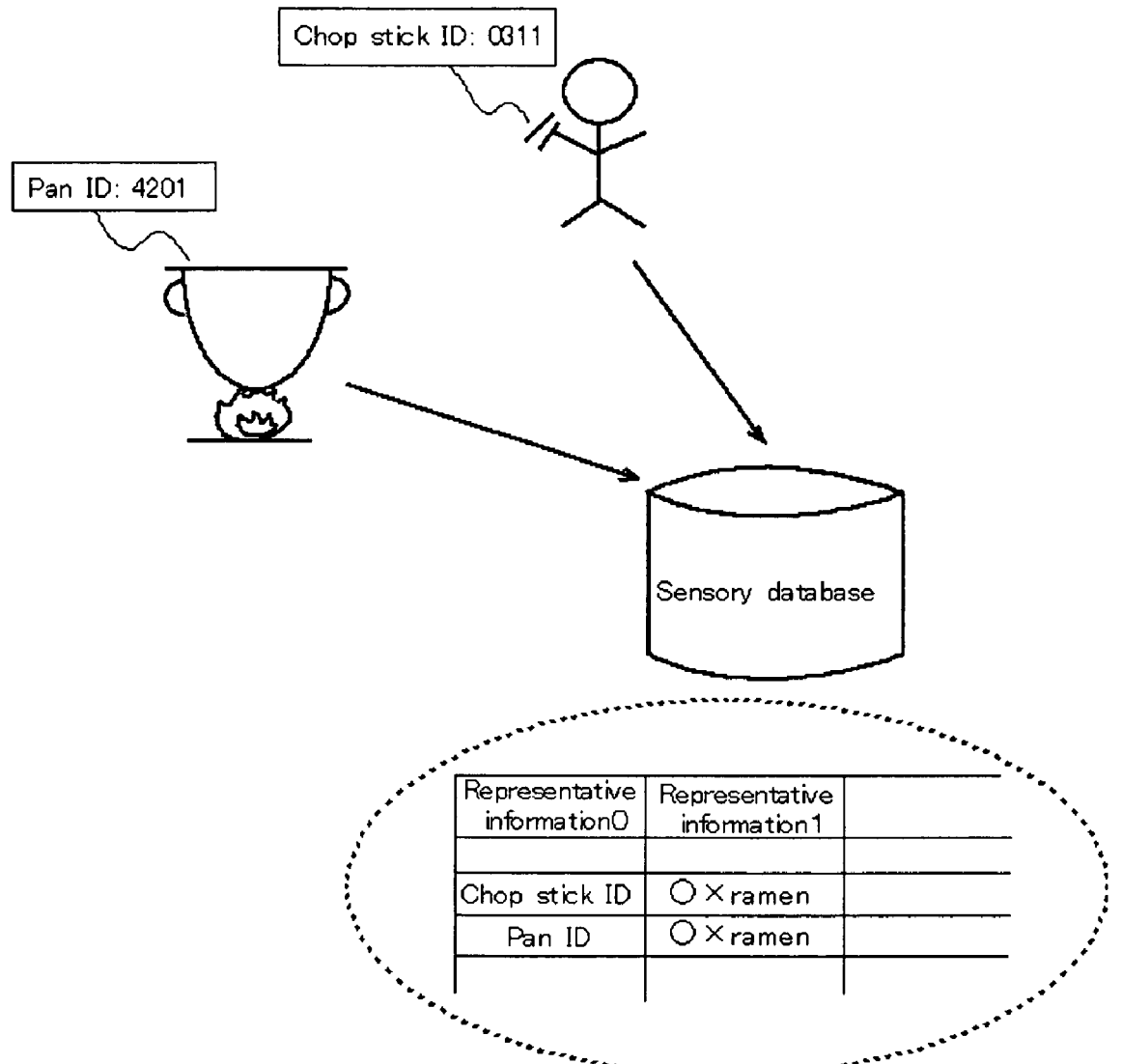
FIG. 14 is a diagram exemplifying a scheme of the sensory database of the fourth embodiment.

FIG. 14 is a diagram exemplifying a scheme of the sensory database of the fourth embodiment. As shown in this diagram, the taste sensor is provided with respective cooking tools such as chopsticks or a pan in the kitchen of the restaurant, and the identification information for cooking tools such as 'chopsticks ID: 0311' or ' pan ID: 4201' is respectively given as the representative information. Then, when these cooking tools are used for cooking, the sensory parameter information, of which the representative information is the identification information for a cooking tool, is acquired and transmitted, and the sensory database receives and stores the information. Thus, for example, in the case of the sensory database of taste, the identification information unique to the sensor provided with respective cooking tools and the sensory parameter information are acquired and stored, or in the case of the database of amusingness of the film, the identification information unique to the sensor provided with respective seats and the sensory parameter information are acquired and stored. Accordingly, the large amount of sensory information of respective cooking tools such as chopsticks or a pan, or of respective seats is acquired and stored according to the measurement result by a sensor, which is common and objective standard, so that it becomes possible to make the database for search based on more objective information.

Figure 15:
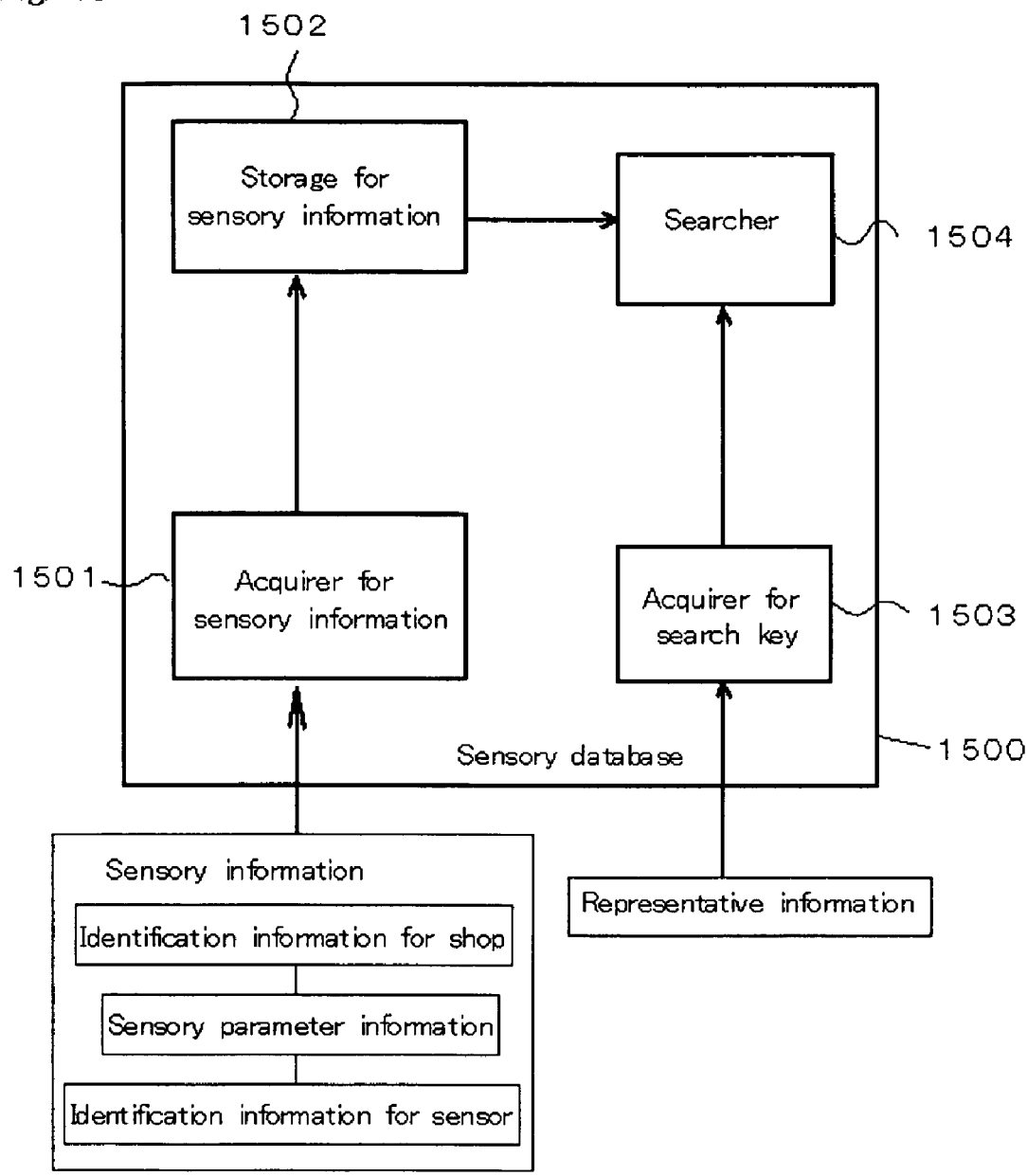
FIG. 15 is a functional block diagram of the sensory database of the fourth embodiment.

FIG. 15 is a functional block diagram of the sensory database of the fourth embodiment. As shown in FIG. 15, the 'sensory database' (1500) of the third embodiment comprises the 'acquirer for sensory information' (1501), the 'storage for sensory information' (1502), the 'acquirer for search key' (1503), and the 'searcher' (1504). Note that, the 'acquirer for search key', and the 'searcher' are the same as those of the first or second embodiment, so that the description thereof will be omitted.

The sensory database of the fourth embodiment is characterized in that the acquirer for sensory information (1501) acquires the sensory information correlated with the identification information for sensor.

The 'identification information for sensor' is information for identification of a sensor. Examples of the information include a production number unique to a sensor, and an IP address unique to a sensor for connecting to the internet.

This identification information for a sensor is given to a sensor provided with respective cooking tools in the kitchen or with respective seats in the cinema, so that it becomes possible to acquire and store large amount of sensory parameter information of respective cooking tools or seats.

Figure 16:
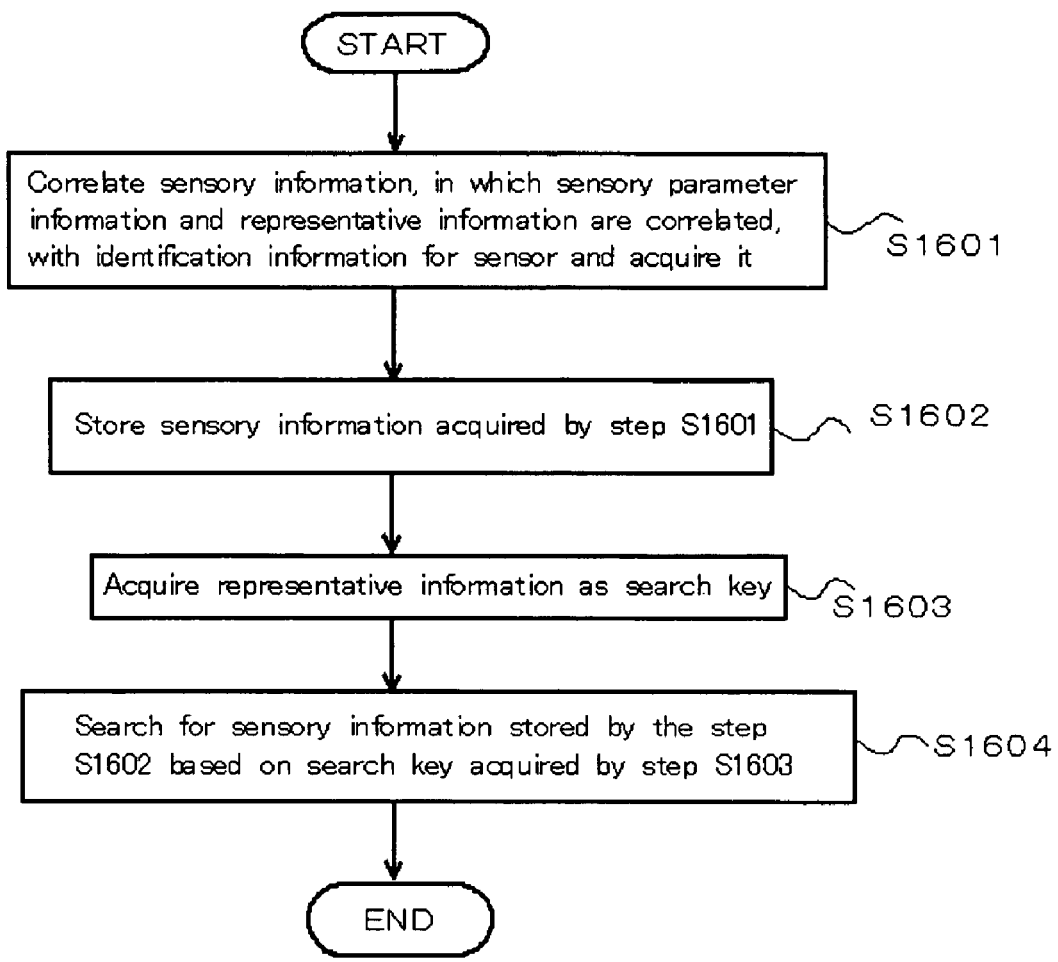
FIG. 16 is a flow chart showing the processing flow of the fourth embodiment.

FIG. 16 is a flow chart showing the processing flow of the fourth embodiment. The processing flow of the fourth embodiment is as follows. At the outset, the sensory information, in which the sensory parameter information and the representative information are correlated, is correlated with the identification information for sensor of the sensor and acquired (step S1601). Subsequently, the sensory information acquired by said step S1601 is stored (step S1602). Then, the representative information is acquired as the search key (step S1603). Finally, the sensory information stored by said step S1602 is searched based on the search key acquired by said step S1603 (step S1604).

According to the sensory database of the fourth embodiment, the large amount of sensory information is acquired and stored according to the measurement result by a sensor, which is a common and objective standard, so that it becomes possible to make the database for search based on more objective information.

The fifth embodiment is the sensory database according to any one of the first to fourth embodiments, wherein the sense is taste, and the sensor is a taste sensor. Therefore, according to the sensory database of the fifth embodiment, for example, based on the taste of ramen or local beer, it becomes possible to search for the restaurant providing the meal having a taste similar to the taste of the meal the user had before. Further, by acquiring and referring to the sensory parameter information of the taste of meal the user wants to cook, it becomes possible to cook the meal having the desired taste.

The sensory database of the fifth embodiment has a configuration similar to that of the sensory database of the first to fourth embodiments, so that the description with reference to the drawings will be omitted. The sensory database of the fifth embodiment is characterized in that the sense is taste, and the sensor is the taste sensor.

The 'taste' is sense of taste caused by the change of the electric potential upon reaction of the taste cell to the taste substance, the parameter of it is indicated based on the change of the electric potential reproduced though simulation by the taste sensor.

The 'taste sensor' is a sensor, as described above, in which the taste substance is received by the multiple lipid polymer membranes imitating a biological membrane of taste cells of the tongue, the respective lipid polymer membranes react to the five taste substances such as bitter taste, sweet taste, acidic taste, flavor, and salty taste, and causes the change of electric potential, and the strength or weakness of the five indications are measured by the change of electric potential. Thus, the change of electric potential actually caused on the sensory cell, not the production of the taste substance, is measured through simulation, thereby acquiring the sensory parameter information of taste as the objective indication.

Figure 17:
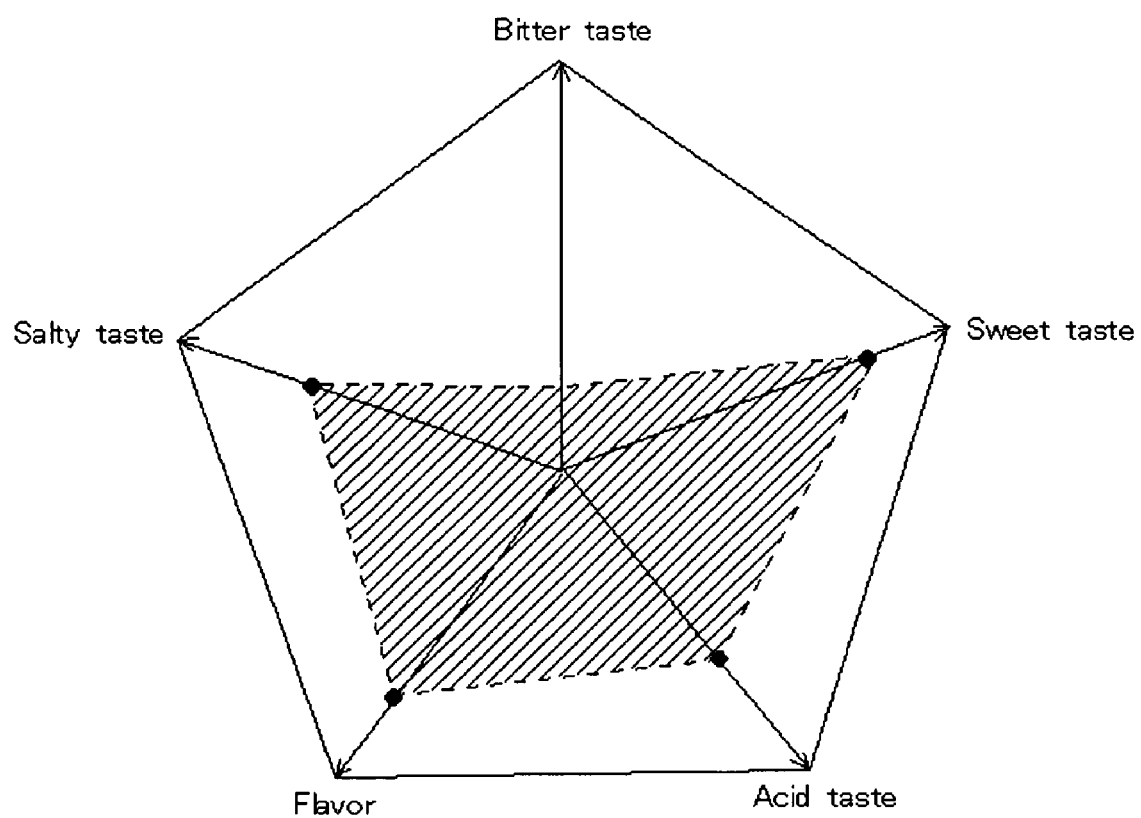
FIG. 17 is a pattern diagram exemplifying the sensory parameter information of taste of the fifth embodiment.

FIG. 17 is a pattern diagram exemplifying the sensory parameter information of taste. As shown in this diagram, as to the sensory parameter information of taste, the five indications such as bitter taste, sweet taste, acidic taste, flavor, and salty taste are given. Now, five types of cells reacting to the taste substances exist in the tongue, and each of them corresponds to the above indications. Therefore, most tastes can be expressed by combinations of these five indications.

Moreover, among the tastes, generally, the 'acidic taste' expresses decay of food, and the 'bitter taste' expresses toxicity. Then, the decay or toxicity of food is measured by the sensor, and the acidic taste or bitter taste is stored in the sensory database of taste, so that it becomes possible to objectively and accurately determine the decay or toxicity of food, which has been determined by conventionally smelling or tasting, using this database for examining.

In addition to the five indications, 'acrid taste', which is taste caused by stimulation to the pain sense of the tongue, may be acquired as the sensory parameter information of taste. This is acquired by the method, in which the change of electric potential of pain sense caused by taste component of acrid taste is measured. Thus, in addition to the five indications composing taste, the 'acrid taste' is acquired as the taste parameter, for example, so that it becomes possible to search for food having similar acrid taste such as kimchi or curry.

As described above, according to the sensory database of taste of the fifth embodiment, for example, it becomes possible to search for the restaurant having the similar taste based on the sensory parameter information of taste, objectively indicated.

In addition, if the parameter of taste includes five parameters such as bitter taste, sweet taste, acidic taste, flavor, and salty taste, it becomes possible to express the emotions equal to the sense (taste) caused by the taste cells of the human tongue. Moreover, it becomes possible to objectively and accurately determine the decay or toxicity of food based on the acidic taste or on the bitter taste.

Furthermore, when the 'acrid taste' is added to the five indications, it becomes possible to carry out a search based on the taste caused not only by the taste cells of the tongue, but also by stimulation of the pain sense.

The sensory database of the sixth embodiment is the sensory database according to the fifth embodiment, wherein identification information of a shop such as 'X ramen shop', identification information of a meal such as 'heavy taste ramen', or the information indicating a feeling after a meal such as 'heavy taste', is acquires as the representative information.

The configuration of the sensory database of the sixth embodiment is the same as that of the fifth embodiment, so that the description with reference to the drawings will be omitted. The sensory database of the sixth embodiment is characterized in that the representative information is the information shown in FIG. 18.

FIG. 18 is a diagram exemplifying the representative information of the sixth embodiment. As shown in this diagram, an example of the representative information includes the identification information of shop for identifying a shop providing foods such as 'X ramen shop', or 'Y-an Shinbashi shop'. Note that the identification information of shop may be name of shop, address or phone number of the shop, or classification number uniquely assigned to respective shops. Thus, by acquiring the identification information of shop as the representative information, it becomes possible to return the search result regarding the shop providing a meal having the sensory parameter information similar to the sensory parameter information as the argument. Alternatively, it becomes possible to return the sensory parameter information the meal provided by the shop by means of the identification information of shop such as name of the shop as the argument.

In addition, another example of the representative information includes the identification information of meal for identifying a meal. As shown in FIG. 18, this representative information may be the name of the meal such as 'salt-based ramen', 'pork and soy sauce-based ramen', or 'Hell ramen', (a combination of) ingredients specific to the meal, or the classification number uniquely assigned to the respective meals.

In addition, another example of the representative information includes the information of feeling after meal, which is information indicating a feeling after eating a meal. As shown in FIG. 18, examples of the information of feeling after a meal may include the term expressing the feeling after a meal such as 'light-taste', 'heavy-taste', or 'super-hot', the symbol indicating the term, or the information indicating degree of satiation such as 'full' or 'less than full'. Note that the information of feeling after a meal is one of the representative information, which is the object of statistical processing described in the third embodiment.

As described above, according to the sensory database of the sixth embodiment, it becomes possible to carry out search based on the name of shop, the name of meal, or the feeling after the meal.

The seventh embodiment is the sensory database according to any one of the first to fourth embodiments, wherein the sense is 'olfactory sense', and the sensor is the 'olfactory sensor'. Therefore, according to the sensory database of the seventh embodiment, for example, it becomes possible to search for an alternative perfume to one's favorite perfume. Further, by acquiring the sensory parameter information of olfactory sense, it becomes possible to blend fragrant materials so that its aroma becomes similar to a favorite aroma.

The configuration of the sensory database of the seventh embodiment is the same as those of the first to fourth embodiments, so that the description with reference to the drawings will be omitted. The sensory database of the seventh embodiment is characterized in that the sense is the olfactory sense, and the sensor is the olfactory sensor.

An example of the 'olfactory sense' includes the 'artificial olfactory sensor using cantilever array' is disclosed as the technology of analyzing atomic filed in surface structure in the website of JPO. In this technology, eight cantilevers are coated with different types of polymers such as PVP, PU, PS, and PMMA as the receptor of smell substance, thereby making the cantilever array. When the cantilever sensor receives the smell substance, according to the smell substance, small deflection is caused, thereby causing an electronic signal. Then, based on the difference in changes of the electronic signals by time-lapse, the object of smell is specified.

Figure 19:
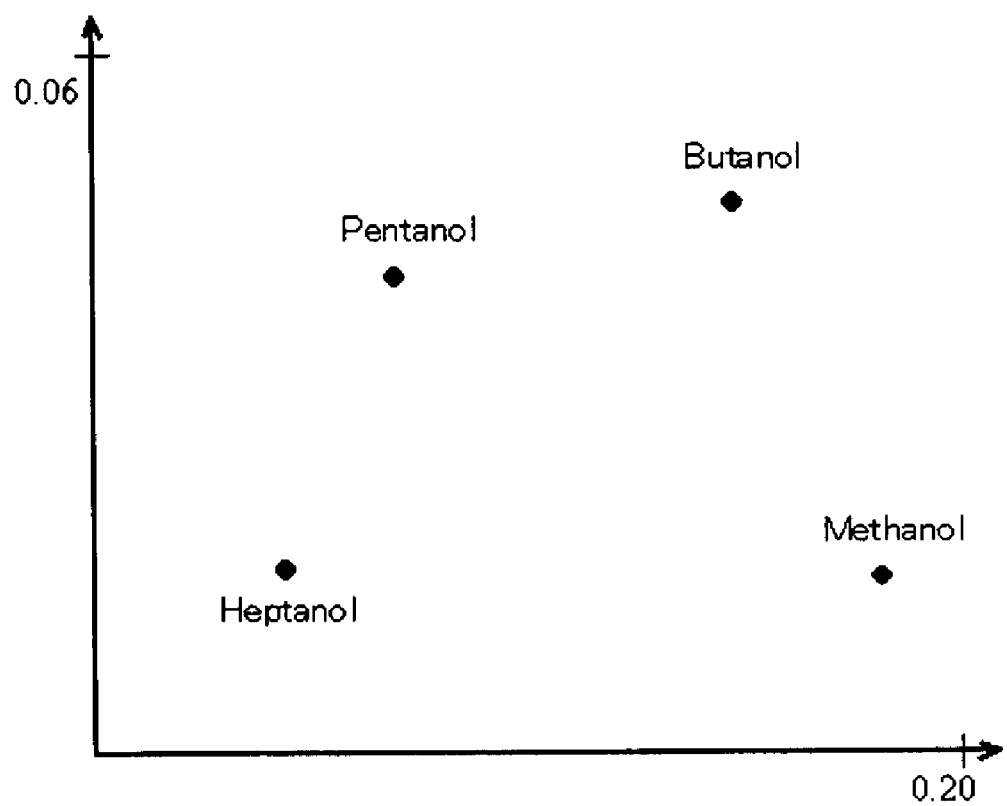
FIG. 19 is a diagram exemplifying smell substances on the PCA plot based on the change in electrical potential by time-lapse measured by a cantilever sensor by means of the olfactory sensor of the seventh embodiment.

FIG. 19 is a diagram exemplifying smell substances on the PCA plot based on the change in electrical potential by time-lapse measured by means of the cantilever sensor. Thus, the change in electrical potential actually caused in the sensory cell according to the smell substance, so that it becomes possible to acquire the sensory parameter information of olfactory sense as an objective indicator.

The acquired sensory parameter information of cosmetics or perfume, and the representative information such as brand name, shop, price, or feeling, are correlated and stored, so that it becomes possible for a user to search for other cosmetic similar to a favorite cosmetic. In addition, the search result is based on the sensory parameter information of olfactory, which is objective, so that the search result is accurate enough, not a classification or a search result based on subjective evaluation of smell.

In addition, as to the smell, the configuration, in which the smells indicating decay or toxicity are stored in the sensory database of the olfactory sense, so that it becomes possible to accurately and objectively judge the decay or toxicity of food, similar to the sensory database of taste, may be used.

As described above, according to the sensory database of the seventh embodiment, for example, it becomes possible to carry out a search for perfume or cosmetic having a similar fragrance based on the sensory parameter information of olfactory, which is objectively indicated.

In addition, by storing the parameter of smell based on the decay or toxicity, it becomes possible to accurately and objectively judge the decay or toxicity.

The eighth embodiment is the sensory database according to any one of the first to fourth embodiments, wherein the sense is a tactile sense, and the sensor is the tactile sensor. Therefore, according to the sensory database of tactile sense of the eighth embodiment, for example, it becomes possible to search for a dentist, whose treatment is objectively determined to be less painful. Moreover, it becomes possible to search for emergency treatment according to pain level. Moreover, by acquiring the sensory parameter information of tactile sense, it becomes possible to objectively check performance of a finger-pressure massager.

The configuration of the sensory database of the eighth embodiment is the same as those of the first to fourth embodiments, so that the description with reference to the drawings will be omitted. The sensory database of the eighth embodiment is characterized in that the sense is the 'tactile sense', and the sensor is the 'tactile sensor'.

The 'tactile sense' is a sense, which is perceived due to a pain-producing substance or electronic signal caused by pressure or stimulation applied to a touch-sensitive spot on skin. For example, pain sense, a sense of pain, or pressure sense, caused by continuously applied pressure.

The 'tactile sensor' is, for example, an apparatus for detecting pressure or displacement applied to the detector, which is composed by means of carbon micro-coil (CMC), as an electronic signal. Further, an example of the tactile sensor may include a sensor detecting pain sense, one of the tactile senses, by detecting production or amount of the pain-producing substance such as histamine.

Figure 20:
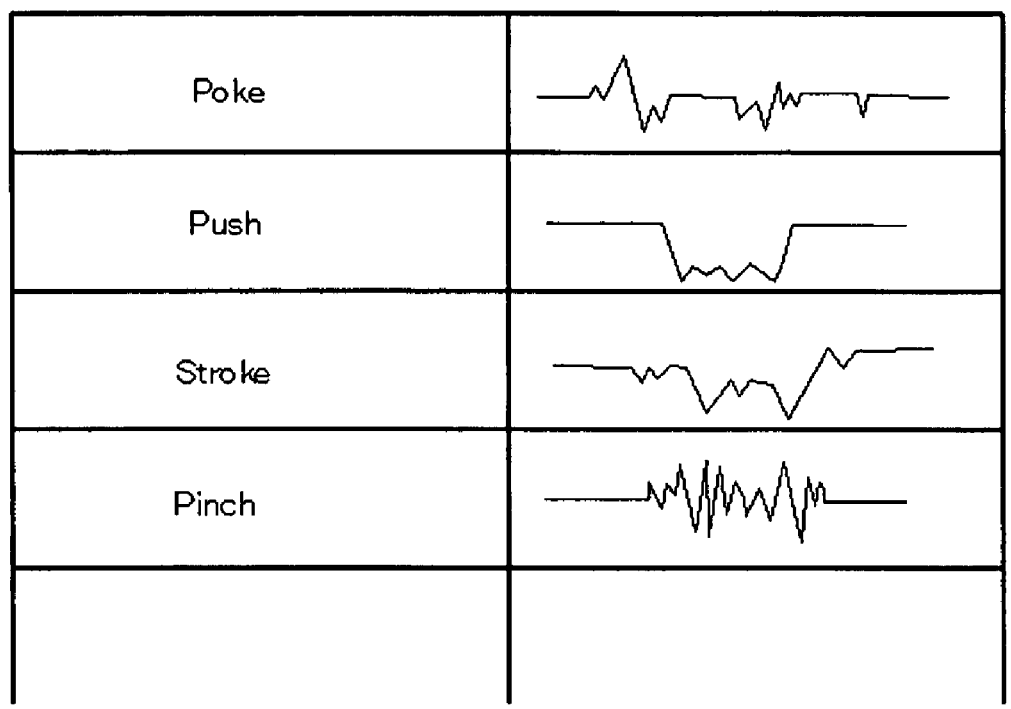
FIG. 20 is a diagram exemplifying types of pressures applied to the tactile sensor by means of the CMC of the eighth embodiment, and the electronic signals detected by the sensor.

FIG. 20 is a diagram exemplifying types of pressures applied to the tactile sensor by means of the CMC, and the electronic signals detected by the sensor. Thus, it is possible to know the details of pressure according to the differences in waves of the electronic signal. Further, according to the amount of the pain-producing substance or to the strength or weakness of the electronic signal, the pain sense may be classified by their level and stored. For example, in cases where the representative information such as the name of dental office or dentist is correlated with the sensory parameter information of pain sense indicating the pain level upon treatment, a user can easily search for a dentist whose treatment skill is objectively determined to be a high level.

In addition, for example, in cases where the parameter information of pain sense, and the treatment method such as soaking a burn under cold water, or cooling a burn with ice are correlated, so that it becomes possible to know the treatment according to the pain level, immediately.

As described above, according to the sensory database of tactile sense of the eighth embodiment, it becomes possible to search for a dentist whose treatment skill is a high level based on the sensory parameter information of tactile sense objectively indicated. In addition, for example, the parameter of pain sense of injury such as a burn or disease, and the level of the injury or disease or the treatment method are correlated and stored, so that it becomes possible to search for the level of the injury or the disease, or the treatment method thereof, immediately.

The ninth embodiment is the sensory database according to any one of the first to fourth embodiment, wherein the sense is 'perception', and the sensor is a 'perception sensor'. Therefore, according to the sensory database of perception of the ninth embodiment, for example, based on the change in brain-waves caused by amusingness of entertainment or an attraction, it becomes possible to search for another entertainment or attraction inducing a similar change in brain-waves.

The configuration of the sensory database of the ninth embodiment is the same as those of the first to fourth embodiments, so that the description with reference to the drawings will be omitted. The sensory database of the ninth embodiment is characterized in that the sense is perception, and the sensor is a perception sensor.

The 'perception' is comprehension of an environmental matter or state based on stimulation received by sense organs. Examples of the perception include emotional changes such as delight, anger, sorrow, and pleasure, fear and awe, or pleasure and displeasure.

The 'biological sensor' is a sensor for detecting the status of perception such as a brain sensor for detecting a type, strength or weakness of perception by measuring brain-waves. In the brain sensor disclosed in Japanese Patent Publication No. H7-204168, a cross-correlation function for three wave patterns of brain-waves ($\theta$-wave, $\alpha$-wave, and $\beta$-wave), and the parameter as state vector are acquired, so that an emotional vector indicating four emotions (delight, anger, sorrow and pleasure) are computed by means of linear conversion. Then, this emotional vector is stored in the sensory database of the ninth embodiment as the sensory parameter information.

FIG. 21 is a diagram exemplifying the emotional vector computed from the electroencephalogram measured by the brain sensor. As shown in this diagram, from the change in brain-waves upon watching the comedy duo B, the emotional vector such as 'stress: 4', 'delight: 6', 'sorrow: 2', and 'relax: 2' is computed. Alternatively, by watching the movie C, the emotional vector such as 'stress: 2', 'delight: 4', 'sorrow: 5', and 'relax: 2' is computed. Therefore, by searching the sensory database of the ninth embodiment by means of the emotional vector, the sensory parameter information, as the search key, it becomes possible to search for another comedian or other entertainment, which causes the user to have the same perception status as that upon watching the comedy duo B or the movie C.

As described above, according to the sensory database of the ninth embodiment, for example, based on the change in brain-waves caused by amusingness of an entertainment or an attraction, it becomes possible to search for another entertainment or attraction inducing similar change in the brain-waves.

Figure 22:
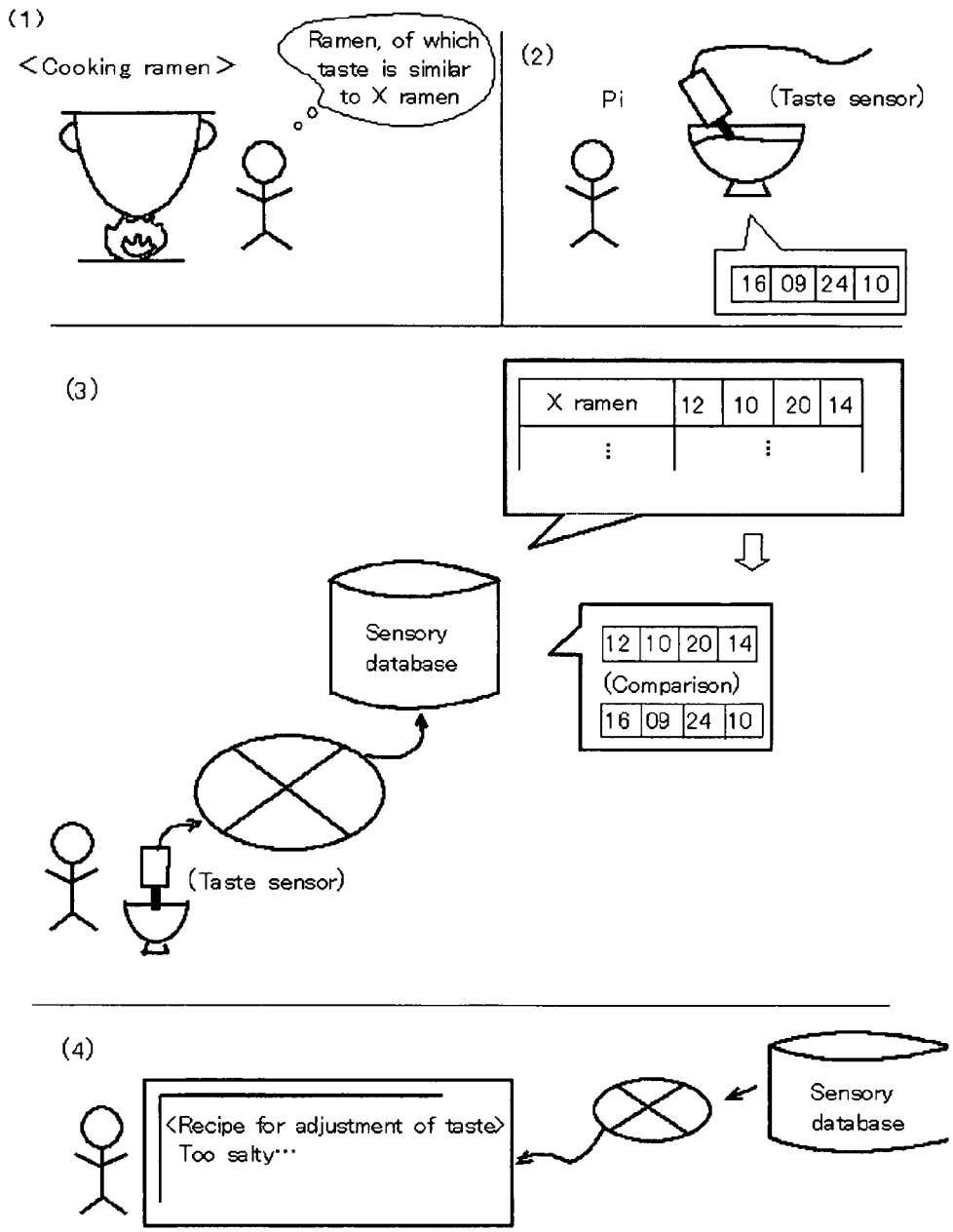
FIG. 22 is a diagram exemplifying the advice of adjustment of taste by means of the sensory database system of the tenth embodiment.

FIG. 22 is a diagram exemplifying the advice of adjustment of taste by means of the sensory database system of the tenth embodiment. As shown in this diagram, a user is cooking ramen at home, which has a taste similar to that of X ramen (1). Then, the user completes cooking the ramen based on the published recipe and on the taste the user remembers. Then, the user measures the sensory parameter information of taste of the ramen '16, 09, 24, 10' by means of the handy-typed taste sensor at home (2). This taste sensor is connected to the sensory database via the internet, and the sensory parameter information of taste measured by the taste sensor is automatically transmitted to the sensory database. Here, when the user inputs 'X ramen' as an example of taste desired by the user, the sensory parameter information of taste of X ramen is searched for based on the search key 'X ramen'. Then, the sensory database compares the sensory parameter information of taste '12, 10, 20, 14', which is the search result, with the sensory parameter information of taste '16, 09, 24, 10', which has been transmitted, thereby determining that it is not salty enough (3). Then, the sensory database transmits the information of advice to the effect that 'it is not salty enough, add 2 g of salt for 100 g of ramen' to the terminal used by the user, and causes the terminal to display the information (4).

As described above, according to the sensory database of the tenth embodiment, it becomes possible for the user to receive the necessary advice to cook the meal having a taste similar to the sensory parameter information of taste stored in the sensory database.

Figure 23:
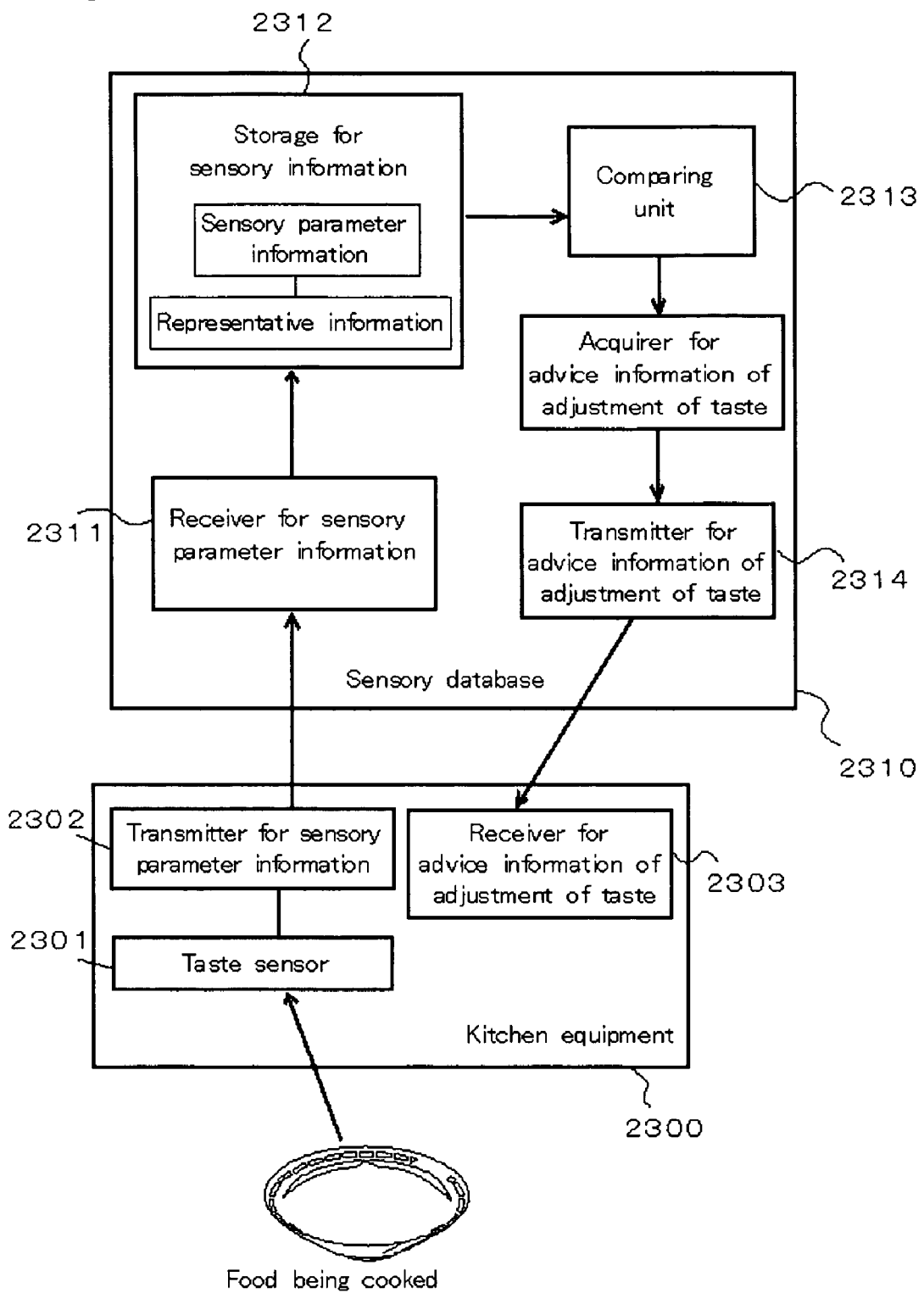
FIG. 23 is a functional block diagram of the sensory database system of the tenth embodiment.

FIG. 23 is a functional block diagram of the sensory database system of the tenth embodiment. As shown in this diagram, the sensory database system of the tenth embodiment comprises the 'kitchen equipment' (2300), and the 'sensory database' (2310).

At the outset, the 'kitchen equipment' (2300) will be described. The 'kitchen equipment' is equipment having the above configuration and is placed in the kitchen. For example, the kitchen equipment may be the taste sensor provided with the internet connection terminal or the external display connection terminal, or may be implemented by the configuration, in which the cooking tools such as chop sticks or a pan has the taste sensor, and is connectable to the display.

In addition, the kitchen equipment comprises the 'taste sensor' (2301), the 'transmitter for sensory parameter information' (2302), and the 'receiver for advice information of adjustment of taste' (2303).

The 'taste sensor' (2301) acquires the sensory parameter indicating taste of food being cooked. An example of the taste sensor includes the aforementioned taste sensor disclosed in Japanese Patent No. 2578370.

The 'transmitter for sensory parameter information' (2302) transmits acquired sensory parameter, which is sensory parameter information acquired by taste sensor (2301), to the sensory database (2310).

The 'receiver for advice information of adjustment of taste' (2303) receives the advice information of adjustment of taste, which is replied based on the acquired sensory parameter information transmitted from the transmitter for sensory parameter information (2302). The 'advice information of adjustment of taste' is the information indicating processes for adjusting taste. Examples of the advice information of adjustment of taste include the information as 'add X g of salt for 100 g of the meal', or the information as 'let the meal stand for X hours'.

Thus, the kitchen equipment acquires and transmits the sensory parameter information of taste of the meal, and receives the advice information of adjustment of taste replied from the sensory database, so that the user can know how to cook the meal having a taste similar to the desired taste.

Note that, as described above, the kitchen equipment may comprise the function of inputting and outputting the representative information for specifying the taste desired by the user.

Subsequently, the 'sensory database' (2310) will be described. The sensory database comprises the 'receiver for sensory parameter information' (2311), the 'storage for sensory information' (2312), the 'comparing unit' (2313), the 'acquirer for advice information of adjustment of taste' (2314), and the 'transmitter for advice information of adjustment of taste' (2315).

Note that the sensory database of the sensory database system of the tenth embodiment is basically the same as the sensory database of taste of the first to fifth embodiments.

The 'receiver for sensory parameter information' (2311) receives the acquired sensory parameter information transmitted from said transmitter for sensory parameter information. Thus, by receiving the acquired sensory parameter information acquired by the taste sensor of the kitchen equipment, it becomes possible to carry out a comparison with the sensory parameter information to be an example of taste, which is stored by it.

The 'storage for sensory information' (2312) stores sensory information. This storage for sensory information is similar to the storage for sensory information described in the first embodiment, and further has the following limitation in order to carry out the comparison to be described hereinbelow. Therefore, the sensory parameter information included in the sensory information to be stored is necessarily acquired by the taste sensor, which is the same as the taste sensor of the kitchen equipment. The reason for this is that the sensory database stores the sensory parameter information measured by the taste sensor, which measures only the 'acrid taste', and the kitchen equipment comprises the taste sensor, which measures the five elements of taste such as 'bitter taste, sweet taste, acidic taste, flavor, and salty taste'. Accordingly, the comparing unit to be described hereinbelow compares the 'acrid taste' with the 'bitter taste, sweet taste, acidic taste, flavor, and salty taste', so that it cannot carry out accurate comparison, and cannot acquire the advice information of adjustment of taste, accurately.

The 'comparing unit' (2313) compares the sensory parameter information correlated with the specific representative information in said storage for sensory information with the acquired sensory information received by said receiver for sensory parameter information.

This comparison may be carried out by the method, in which if the sensory parameter information is indicated by mutually independent numeric values of bitter taste, sweet taste, acidic taste, flavor, or salty taste, respectively, the difference of the numeric values are acquired respectively, and are compared respectively. Alternatively, the method for comparing, in which the difference in values is acquired by correlating the values considering a synergic effect in which a small increase of salty taste enhances a sweet taste etc., may be used.

In addition, selection of the sensory parameter information to be compared with this acquired sensory parameter information may be carried out based on the representative information for specifying the sensory parameter information transmitted from the kitchen equipment as described above. Alternatively, if there is no transmission of this representative information, the configuration, in which the sensory database proposes the name of the meal having the sensory parameter information of taste, which is similar to the acquired sensory parameter information, and causes the user to select, or the configuration, in which the sensory database automatically selects the sensory parameter information to be compared according to the history information etc., may be used.

The 'acquirer for advice information of adjustment of taste' (2314) acquires advice information of adjustment of taste based on the comparative result by said comparing unit. This acquisition of the advice information of adjustment of taste by the acquirer for advice information of adjustment of taste may be implemented by the method, in which the data table correlating the comparative result and the advice information of adjustment of taste is preliminarily stored.

FIG. 24 is a pattern diagram exemplifying the acquisition of the advice information of adjustment of taste by the acquirer for advice information of adjustment of taste. As shown in this diagram, in the comparing unit, the difference of the numeric values of salty taste and sweet taste as the sensory parameter information is computed. Here, the sensory database preliminarily stores the seasoning data, in which the seasoning and the effects are correlated. Then, the acquirer for advice information of adjustment of taste computes the amount of necessary seasoning according to the difference in values and the seasoning data, and generates and acquires the advice information of adjustment of taste. For example, if the difference value of salty taste is '4', the information 'salt, 4% of the total amount' is computed.

Similarly, the comparison may be carried out with reference to the information table for advising adjustment of taste other than for the seasoning, which is stored in the sensory database. In this information table, for example, the information indicating that curry, left for X hours at normal temperature, increases Y point of sweet taste is stored, and the advice information of adjustment of taste indicating that 'leave it for 2 hours' is acquired according to the comparative result by the comparing unit.

Alternatively, in the sensory database, for example, the sample sensory parameter information of several patterns of seasoning for the original X ramen, and the pattern of seasoning may be correlated and stored. Then, the sample sensory parameter information of X ramen, which is similar to the acquired sensory parameter information, is extracted from the sample sensory parameter information, and the pattern of seasoning, which has been correlated with it, is acquired. Then, the short or excessive seasoning and the amount of it are computed according to the pattern of seasoning, so that the advice information of adjustment of taste may be generated and acquired.

Figure 25:
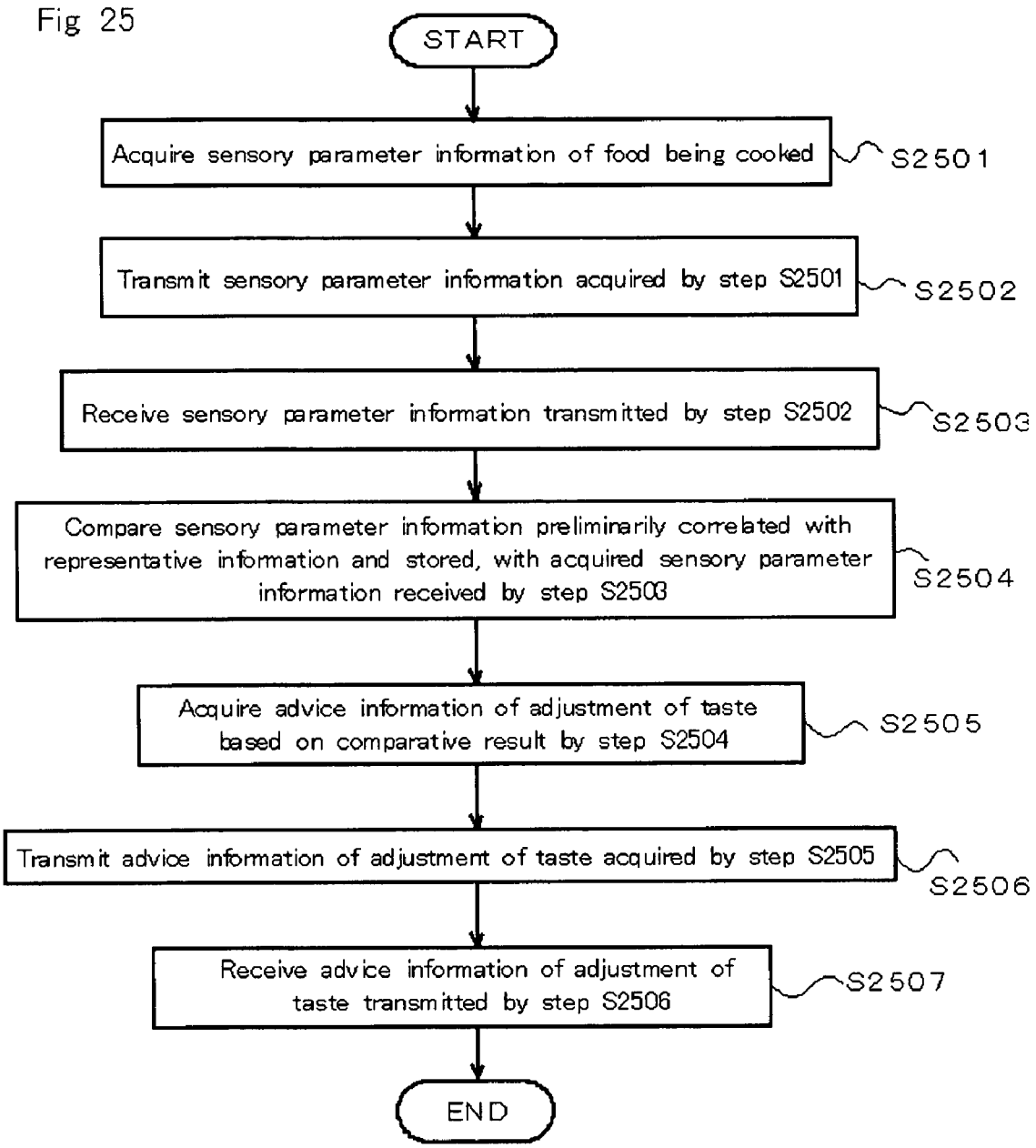
FIG. 25 is a flow chart showing a processing flow of the tenth embodiment.

The 'transmitter for advice information of adjustment of taste' (2315) transmits the advice information of adjustment of taste acquired by said acquirer for advice information of adjustment of taste to said kitchen equipment. By the advice information of adjustment of taste thus transmitted, the user can know how to cook the meal having a taste similar to the desired taste. FIG. 25 is a flow chart showing a processing flow of the tenth embodiment. The processing flow of the tenth embodiment is as follows. At the outset, the sensory parameter information of food being cooked is acquired (step S2501). Subsequently, the sensory parameter information acquired by step S2501 is transmitted (step S2502). Subsequently, the sensory parameter information transmitted by step S2502 is received (step S2503). Further, the sensory parameter information preliminarily correlated with the representative information and stored, and the acquired sensory parameter information received by the step S2503 are compared (step S2504). Further, the advice information of adjustment of taste based on the comparative result by step S2504 is acquired (step S2505). Furthermore, the advice information of adjustment of taste acquired by step S2505 is transmitted (step S2506). Finally, the advice information of adjustment of taste transmitted by step S2506 is received (step S2507).

As described above, according to the sensory database of the tenth embodiment, it becomes possible for the user to receive the necessary advice to cook the meal in the kitchen having the taste similar to the sensory parameter information of taste stored in the sensory database.

What is claimed is:

1. A sensory database system, comprising:
   a kitchen equipment; and
   a sensory database, wherein said kitchen equipment comprises:
   a taste sensor, which acquires sensory parameter information indicating taste of food being cooked,
   a transmitter for sensory parameter information, which transmits acquired sensory parameter information, which is sensory parameter information acquired by said taste sensor, to said sensory database, and
   a receiver for advice information of adjustment of taste, which receives advice information of adjustment of taste, which is replied based on the acquired sensory parameter information transmitted from said transmitter for sensory parameter information, and said sensory database comprises:

a receiver for sensory parameter information, which receives the acquired sensory parameter information transmitted from said transmitter for sensory parameter information, a storage for sensory information, which stores sensory information, in which sensory parameter information indicating sense acquired by a taste sensor, which is same type of sensor as said taste sensor, and representative information representing the sense are correlated, a comparing unit, which compares the sensory parameter information correlated with the specific representative information in said storage for sensory information with the acquired sensory parameter information received by said receiver for sensory parameter information, an acquirer for advice information of adjustment of taste, which acquires advice information of adjustment of taste based on the comparative result by said comparing unit, and a transmitter for advice information of adjustment of taste, which transmits the advice information of adjustment of taste acquired by said acquirer for advice information of adjustment of taste to said kitchen equipment.

2. A method for advising adjustment of taste by means of sensory database system, comprising:

a step of acquiring sensory parameter, which acquires sensory parameter information indicating taste of food being cooked;

a step of transmitting sensory parameter information, which transmits acquired sensory parameter information, which is sensory parameter information acquired by said step of acquiring sensory parameter;

a step of receiving acquired sensory parameter information, which receives the sensory parameter information transmitted by said step of transmitting sensory parameter information;

a step of comparing, which compares sensory parameter information, which has preliminarily been correlated with the specific representative information and has been stored, with the acquired sensory parameter information, which is sensory parameter information received by said step of receiving acquired sensory parameter information;

a step of acquiring advice information of adjustment of taste, which acquires advice information of adjustment of taste based on the comparative result by said step of comparing;

a step of transmitting advice information of adjustment of taste, which transmits the advice information of adjustment of taste acquired by said step of acquiring advice information of adjustment of taste; and a step of receiving advice information of adjustment of taste, which receives the advice information of adjustment of taste replied by said step of transmitting advice information of adjustment of taste.

* * * * *